(12) United States Patent
Shiba

(10) Patent No.: US 8,158,775 B2
(45) Date of Patent: Apr. 17, 2012

(54) METHOD FOR DETACHING PROTECTING GROUP ON NUCLEIC ACID

(75) Inventor: Yoshinobu Shiba, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 576 days.

(21) Appl. No.: 12/280,764

(22) PCT Filed: Feb. 26, 2007

(86) PCT No.: PCT/JP2007/053490
§ 371 (c)(1),
(2), (4) Date: Oct. 21, 2008

(87) PCT Pub. No.: WO2007/099896
PCT Pub. Date: Sep. 7, 2007

(65) Prior Publication Data
US 2009/0149645 A1 Jun. 11, 2009

(30) Foreign Application Priority Data
Feb. 27, 2006 (JP) ................... 2006-050381

(51) Int. Cl.
*C07H 21/02* (2006.01)
(52) U.S. Cl. .................................. 536/25.31
(58) Field of Classification Search .............. None
See application file for complete search history.

(56) References Cited

U.S. PATENT DOCUMENTS

| | | | |
|---|---|---|---|
| 6,413,732 B1* | 7/2002 | Kahne et al. | 435/15 |
| 6,703,213 B2* | 3/2004 | Kahne et al. | 435/15 |
| 2002/0182661 A1 | 12/2002 | Kahne et al. | |
| 2007/0282097 A1* | 12/2007 | Ohgi et al. | 536/23.1 |
| 2009/0137790 A1* | 5/2009 | Enya | 536/25.33 |
| 2009/0312534 A1* | 12/2009 | Kitagawa et al. | 536/25.34 |

FOREIGN PATENT DOCUMENTS

| | | |
|---|---|---|
| EP | 693287 | 1/1996 |
| WO | WO-2005/023828 | 3/2005 |
| WO | WO-2006/095739 | 9/2006 |

OTHER PUBLICATIONS (R) Umemoto et al., "Oligoribonucleotide Synthesis by the Use of 1-(2-cyanoethoxy)ethyl (CEE) as a 2'-Hydroxy Protecting Group," Tetrahedron Letters, 45(52), 9529-9531 (publ. online Nov. 11, 2004).*
Ohgi T. et al. ,A New RNA Synthetic Method 1-23 With A 2'-O-(2-Cyanoethoxymethyl) Protecting Group. / Org Lett. / 2005/ vol. 7, No. 16, p. 3477-3480.
Sinha ND et al./Polymer Support Oligonucleotide Synthesis XVIII: Use of Beta-Cyanoethyl-N, N-Dialkylamino-/N-Morpholino Phosphoramidite of Deoxynucleosides for the Synthesis of DNA Fragments Simplifying Deprotection and Isolation of the Final Product., Nucleic Acids Res. 1984;12 (11) :4539-4557.
L.A. Ramos et al./Carboxymethylation of Cellulose in the New Solvent Dimethyl Sulfoxide/Tetrabutylammonium Fluoride, Carbohydrate Polymers ,vol. 60/ Issue Feb. 2005/ pp. 259-267.
Brian C. Froehler. Chapter 4: Oligodeoxynucleotide Synthesis. H-Phosphonate Approach. Methods in Molecular Biology, vol. 20: Protocols for Oligonucleotides and Analogs. Edited by: S. Agrawal. 1993. Human Press Inc., Totawa, NJ.

* cited by examiner

*Primary Examiner* — Lawrence E Crane
(74) *Attorney, Agent, or Firm* — McDermott Will & Emery LLP

(57) ABSTRACT

The present invention provides a method for removing a 2-cyanoethoxymethyl (CEM) group, which substitutes the 2'-hydroxyl group of each ribose of an oligonucleic acid derivative, with good reproducibility and high efficiency. The present invention further provides a method for producing an oligonucleic acid derivative represented by the following general formula (11), characterized by using a sulfoxide-based solvent or an amide-based solvent or a mixture thereof as a reaction solvent in the step of removing a protecting group, which protects the 2'-hydroxyl group of each ribose of an oligonucleic acid derivative represented by the following general formula (10) by allowing TBAF to act on the oligonucleic acid derivative.

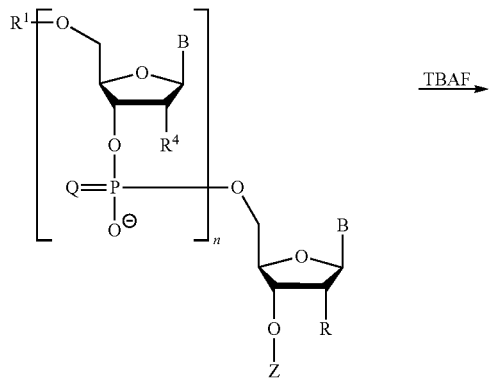

(10)

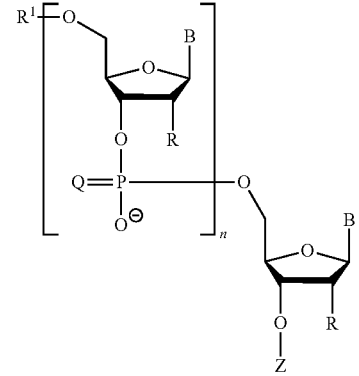

(11)

17 Claims, No Drawings

SEQUENCE LISTING

<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Synthetic Nucleic Acid

<400> SEQUENCE: 1

```
uuuuuuuuuu uuuuuuuuu u                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 2
cuuacgcuga guacuucgat t                                             21

<210> SEQ ID NO 3
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 3
acugacugac ugacugacug acugt                                         25

<210> SEQ ID NO 4
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 4
acugacugac ugacugacug t                                             21
```

METHOD FOR DETACHING PROTECTING GROUP ON NUCLEIC ACID

CROSS-REFERENCE TO RELATED APPLICATIONS

This is the U.S. national phase application under 35 U.S.C. §371 of International Patent Application No. PCT/JP2007/053490, filed Feb. 26, 2007, and claims the benefit of Japanese Patent Application No. 2006-050381, filed Feb. 27, 2006. Both the international and priority applications are incorporated by reference herein in their entirety. The International Application published in Japanese on Sep. 7, 2007 as International Publication No. WO 2007/099896 A1 under PCT Article 21(2).

FIELD OF THE INVENTION

The present invention relates to a method for removing an ether-type protecting group, which protects the 2'-hydroxyl group of each ribose of an oligonucleic acid derivative and can be removed under neutral conditions, such as 2-cyanoethoxymethyl (hereinafter referred to as the "CEM group") with good reproducibility and high efficiency.

BACKGROUND ART

It is well known that an oligoribonucleic acid (oligo-RNA) is useful as a RNA probe for genetic analysis, a material for a RNA drug product (an antisense RNA, a ribozyme, or an RNA species that regulates gene expression through the RNAi effect), an artificial enzyme, or an aptamer.

As one of the reagents for producing an oligo-RNA, a phosphoramidite compound in which the 2'-hydroxyl group of a ribose is protected by substitution by a CEM group which can be removed under neutral conditions is known (Non-patent document 1).

In cases where an oligo-RNA is produced by using the above-mentioned phosphoramidite compound, after an oligo-RNA having a desired chain length is produced on a solid-phase support, it is necessary to remove the oligo-RNA from the solid-phase support and to remove the protecting group for each substituent from the oligo-RNA. One of the steps of removing such a protecting group is the step of removing an ether-type protecting group, which protects the 2'-hydroxyl group of each ribose of an oligo-RNA and can be removed under neutral conditions. In the step, tetrabutylammonium fluoride (hereinafter referred to as "TBAF") is generally used as a deprotecting agent, and tetrahydrofuran (hereinafter referred to as "THF") is used as a solvent (Non-patent document 1).

Non-patent document 1: Ohgi et al., Organic Letters, Vol. 7, 3477 (2005)

DISCLOSURE OF THE INVENTION

Problem to be Solved by the Invention

The main object of the present invention is to provide a method for removing an ether-type protecting group, which protects the 2'-hydroxyl group of each ribose of an oligonucleic acid derivative and can be removed under neutral conditions with good reproducibility and high efficiency.

Means to Solve the Problem

As a result of extensive studies for achieving the above object, the present inventor has found that an oligonucleic acid derivative represented by the following general formula (11) can be efficiently produced by using a sulfoxide-based solvent or an amide-based solvent or a mixture thereof, each of which may contain THF, as a reaction solvent in the step of removing an ether-type protecting group, which protects the 2'-hydroxyl group of each ribose of an oligonucleic acid derivative represented by the following general formula (10) and can be removed under neutral conditions, by allowing TBAF to act on the oligonucleic acid derivative, and thus the present invention has been completed.

[CHEMICAL 1]

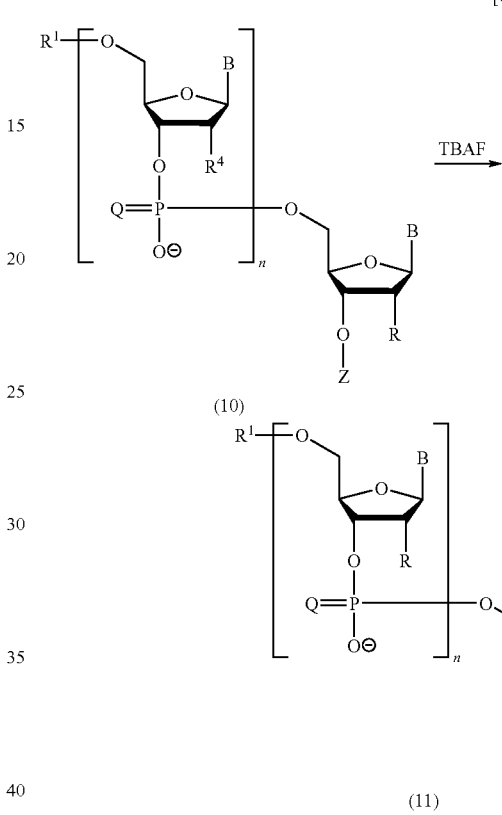

In the general formulae (10) and (11), each B independently represents a nucleobase or a modified form thereof. n represents an integer in the range of 1 to 200. n represents preferably an integer in the range of 10 to 100, and more preferably an integer in the range of 15 to 50. Each Q independently represents O or S. Each R independently represents H, hydroxyl, halogen, alkoxy, alkylthio, alkylamino, dialkylamino, alkenyloxy, alkenylthio, alkenylamino, dialkenylamino, alkynyloxy, alkynylthio, alkynylamino, dialkynylamino or alkoxyalkyloxy, and at least one R represents hydroxyl. Z represents H, a phosphate group or a thiophosphate group. $R^1$ represents a substituent represented by the following general formula (3).

[CHEMICAL 2]

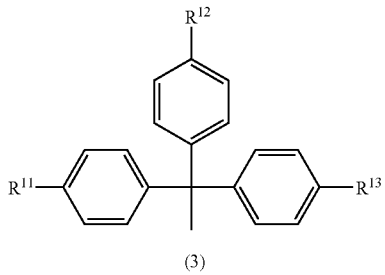

(3)

In the general formula (3), $R^{11}$, $R^{12}$ and $R^{13}$ are the same or different and each represents hydrogen or alkoxy.

Each $R^4$ independently represents H, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or a substituent represented by the following general formula (4).

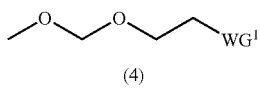

[CHEMICAL 3]

(4)

In the general formula (4), $WG^1$ represents an electron-withdrawing group.

The "nucleobase" represented by B is not particularly limited and examples thereof may include pyrimidine bases such as cytosine, uracil and thymine, purine bases such as adenine and guanine.

The "modified form" of B is a group in which a nucleobase has been substituted by an arbitrary substituent. Examples of the substituent may include halogen, acyl, alkyl, arylalkyl alkoxy, alkoxyalkyl, hydroxyl, amino, monoalkylamino, dialkylamino, carboxy, cyano and nitro. The modified form of B may be substituted by 1 to 3 of these substituents at arbitrary positions.

Examples of the "halogen" related to the modified form of B may include fluorine, chlorine, bromine and iodine.

Examples of the "acyl" related to the modified form of B may include straight or branched alkanoyl having 1 to 6 carbon atoms and aroyl having 7 to 13 carbon atoms. Specifically, the acyl may include, for example, formyl, acetyl, n-propionyl, isopropionyl, n-butyryl, isobutyryl, tert-butyryl, valeryl, hexanoyl, benzoyl, naphthoyl and levulinyl.

Examples of "alkyl" related to the modified form of B may include straight or branched alkyl having 1 to 5 carbon atoms. Specifically, the alkyl may include, for example, methyl, ethyl, n-propyl, isopropyl, n-butyl, isobutyl, sec-butyl, tert-butyl, n-pentyl, isopentyl, neopentyl, and tert-pentyl. The alkyl may be substituted and examples of the "substituent" may include halogen, alkyl, alkoxy, cyano and nitro. The alkyl may be substituted by 1 to 3 of these substituents at arbitrary positions.

Examples of the "alkyl" moiety of the "arylalkyl", "alkoxyalkyl", "monoalkylamino" and "dialkylamino" related to the modified form of B may include the same ones as those illustrated for the above-mentioned "alkyl".

Examples of the "alkoxy" related to the modified form of B may include straight or branched alkoxy having 1 to 4 carbon atoms. Specifically, the alkoxy may include, for example, methoxy, ethoxy, n-propoxy, isopropoxy, n-butoxy, isobutoxy, sec-butoxy and tert-butoxy. Among these, alkoxy groups having 1 to 3 carbon atoms are preferable, and methoxy is more preferable.

Examples of the "alkoxy" moiety of the "alkoxyalkyl" related to the modified form of B may include the same ones as those illustrated for the above-mentioned "alkoxy".

Examples of the "aryl" moiety of the "arylalkyl" related to the modified form of B may include aryl groups having 6 to 12 carbon atoms. Specifically, the aryl may include, for example, phenyl, 1-naphthyl, 2-naphthyl and biphenyl. The aryl may be substituted, and examples of the "substituent" may include halogen, alkyl, alkoxy, cyano, and nitro. The aryl may be substituted by 1 to 3 of these substituents at arbitrary positions.

Examples of the "halogen", "alkyl" or "alkoxy", which are substituents of the alkyl and aryl related to the modified form of B may include the same ones as those illustrated in the above description, respectively.

Examples of the "halogen", "alkoxy", "alkylamino" or "dialkylamino" related to R and $R^4$ may include the same ones as those related to the above-mentioned modified form of B.

Examples of the "alkyl" moiety of the "alkoxyalkyloxy" or "alkylthio" related to R and $R^4$ may include the same ones as the "alkyl" related to the above-mentioned modified form of B.

Examples of the "alkoxy" moiety of the "alkoxyalkyloxy" of R and $R^4$ may include the same ones as the "alkoxy" related to the above-mentioned modified form of B.

Examples of the "alkenyl" moiety of the "alkenyloxy", "alkenylthio", "alkenylamino" or "dialkenylamino" related to R and $R^4$ may include straight or branched alkenyl having 2 to 6 carbon atoms. Specifically, the alkenyl may include, for example, vinyl, allyl, 1-propenyl, isopropenyl, 1-butenyl, 2-butenyl, 1-pentenyl and 1-hexenyl.

Examples of the "alkynyl" moiety of the "alkynyloxy", "alkynylthio", "alkynylamino" or "dialkynylamino" related to R and $R^4$ may include straight or branched alkynyl having 2 to 4 carbon atoms. Specifically, the alkynyl may include, for example, ethynyl, 2-propynyl and 1-butynyl.

Examples of the "alkoxy" related to $R^{11}$, $R^{12}$ and $R^{13}$ may include the same ones as the "alkoxy" related to the above-mentioned modified form of B.

Examples of the "electron-withdrawing group" of $WG^1$ may include, for example, cyano, nitro, alkylsulfonyl, arylsulfonyl and halogen. Among them, cyano is preferred.

Examples of the "alkyl" moiety of the "alkylsulfonyl" of $WG^1$ may include the same ones as the "alkyl" related to the above-mentioned modified form of B.

Examples of the "aryl" moiety of the "arylsulfonyl" of $WG^1$ may include the same ones as the "aryl" related to the above-mentioned modified form of B.

Examples of the "sulfoxide-based solvent" may include a compound represented by the following general formula (1). Specifically, the sulfoxide-based solvent may include, for example, dimethylsulfoxide (hereinafter referred to as "DMSO") and ethyl methyl sulfoxide. Among them, DMSO is appropriate.

Examples of the "amide-based solvent" may include a compound represented by the following general formula (II). Specifically, the amide-based solvent may include, N,N-dimethylformamide (hereinafter referred to as "DMF"), N,N-diethylformamide, N,N-dimethylacetamide, N,N-diethylacetamide and N-methylpyrrolidone. Among them, DMF is appropriate.

[CHEMICAL 4]

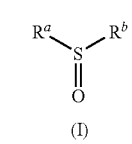

(I)

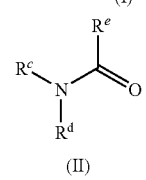

(II)

In the general formulae (I) and (II), $R^a$ and $R^b$ are the same or different and each represents alkyl. $R^c$ and $R^d$ are the same or different and each represents alkyl, and $R^e$ represents hydrogen or alkyl; or $R^d$ represents alkyl, and $R^c$ and $R^e$ represent a 5- or 6-membered saturated cyclic amide group when combined together with the adjacent nitrogen atom and carbon atom.

Further, as the present invention, a method for producing an oligo-RNA represented by the following general formula (A) (hereinafter referred to as an "oligo-RNA (A)") comprising the step of producing an oligonucleic acid derivative represented by the following general formula (11), characterized by using a sulfoxide-based solvent, an amide-based solvent or a mixture thereof, each of which may contain THF, as a reaction solvent in the step of removing an ether-type protecting group, which protects the 2'-hydroxyl group of each ribose of an oligonucleic acid derivative represented by the following general formula (10) and can be removed under neutral conditions, by allowing TBAF to act on the oligonucleic acid derivative can be exemplified.

[CHEMICAL 5]

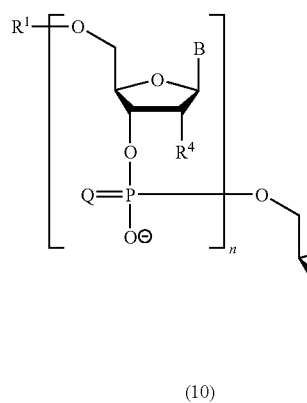

(10)

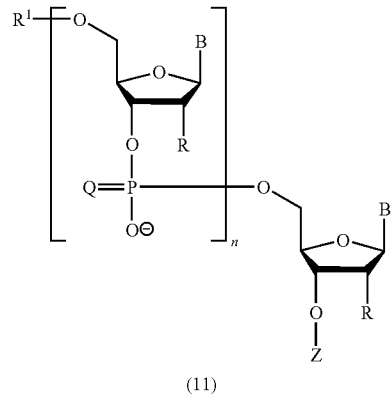

(11)

In the general formulae (10) and (11), each B, each Q, each R, and each $R^4$ independently have the same meanings as above, and n, $R^1$ and Z have the same meanings as above.

[CHEMICAL 6]

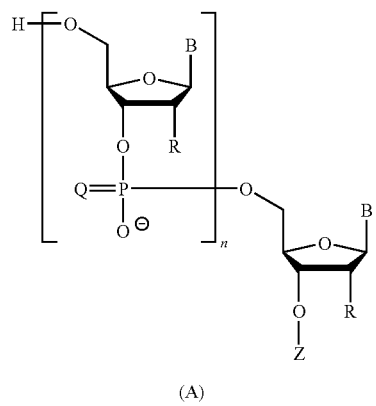

(A)

In the general formula (A), each B, each Q, and each R independently have the same meanings as above, and n and Z have the same meanings as above.

Hereinafter, the present invention will be described in detail.

I. A Phosphoramidite Compound

As the ribonucleic acid derivative to be used in the production of the above-mentioned oligo-RNA (A), a phosphoramidite compound represented by the following general formula (B) (hereinafter referred to as a "phosphoramidite compound (B)") can be exemplified.

[CHEMICAL 7]

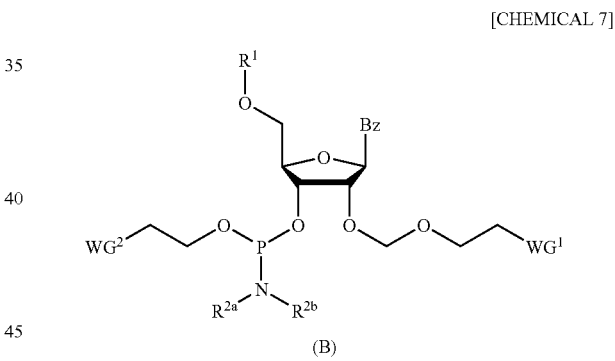

(B)

In the general formula (B), B, represents a nucleobase which may have a protecting group or a modified form thereof. $R^1$ and $WG^1$ have the same meanings as above. $WG^2$ represents an electron-withdrawing group. $R^{2a}$ and $R^{2b}$ are the same or different and each represents alkyl, or $R^{2a}$ and $R^{2b}$ may form a 5- or 6-membered saturated cyclic amino group when combined together with the adjacent nitrogen atom. The saturated cyclic amino group may have one oxygen atom or one sulfur atom as a ring-composing member in addition to the nitrogen atom.

Examples of the "nucleobase" related to $B_Z$ is not particularly limited as long as it is a nucleobase to be used in the synthesis of a nucleic acid, and may include, for example, pyrimidine bases such as cytosine and uracil, purine bases such as adenine and guanine.

The "nucleobase" related to $B_Z$ may be protected, and particularly in the case of a nucleobase having an amino group such as adenine, guanine or cytosine, the amino group thereof is preferably protected.

The "protecting group of amino group" is not particularly limited as long as it is a protecting group to be used as a protecting group of a nucleic acid, and may include, for example, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene.

The "modified form" related to $B_Z$ is the group in which a nucleobase has been substituted with an arbitrary substituent. Examples of "substituent" related to the "modified form" of $B_Z$ may include halogen, acyl, alkyl, arylalkyl, alkoxy, alkoxyalkyl, hydroxyl, amino, monoalkylamino, dialkylamino, carboxy, cyano and nitro. The modified form of $B_Z$ may be substituted by 1 to 3 of these substituents at arbitrary positions.

Examples of the "halogen", "acyl", "alkyl", "arylalkyl", "alkoxy", "alkoxyalkyl", "monoalkylamino" or "dialkylamino" related to the modified form of $B_Z$ may include the same ones as those related to the above-mentioned modified form of B.

Examples of the "alkyl" of $R^{2a}$ and $R^{2b}$ may include the same ones as the "alkyl" related to the above-mentioned modified form of B Examples of the "5- or 6-membered saturated cyclic amino group" of $R^{2a}$ and $R^{2b}$ may include pyrrolidin-1-yl, piperidin-1-yl, morpholin-1-yl and thiomorpholin-1-yl.

Examples of the "electron-withdrawing group" of $WG^2$ may include the same ones as those illustrated for the electron-withdrawing group related to the above-mentioned $WG^1$.

The phosphoramidite compound (B) is a phosphoramidite compound having an ether-type protecting group at the 2'-hydroxyl position, which can be removed under neutral conditions.

Further, a group introduced into the 2'-hydroxyl group is a linear substituent and the steric structure around a phosphorus atom which binds to the 3'-hydroxyl group is not crowded. Therefore, the phosphoramidite compound (B) has a feature that when an oligo-RNA is synthesized, it allows a condensation reaction to proceed in a much shorter time and has a higher condensation yield in comparison with a conventionally used phosphoramidite compound. By using the phosphoramidite compound (B), a high purity oligo-RNA (A) can be produced with the substantially same method as that for the production of an oligo-DNA.

The "oligo-DNA" as used herein refers to an oligonucleic acid composed only of a deoxyribonucleic acid (DNA). Further, the "oligo-RNA" in the present invention refers to an oligonucleic acid which is composed of a ribonucleic acid (RNA) and a deoxyribonucleic acid (DNA) and contains at least one ribonucleic acid.

BEST MODE FOR CARRYING OUT THE INVENTION

In the following production method, it is common, when raw materials have a substituent that affects the reaction (e.g., hydroxyl, amino and carboxy), the reaction is carried out after the raw materials are protected with a suitable protecting group according to a known method. After the reaction is completed, the protecting group can be removed by a known method such as catalytic reduction, alkali treatment, acid treatment or the like.

II. Method of Producing the Phosphoramidite Compound (B)

The phosphoramidite compound (B) can be produced as follows.

The phosphoramidite compounds (B) can be produced from a known compound or an intermediate which can easily be produced through the following steps a to h, for example.

The method of producing the phosphoramidite compound (B) is described in detail below.

(1) Step a:

Process for producing a ribonucleoside derivative represented by the following general formula (13), wherein an ether-type protecting group which can be removed under neutral conditions is introduced to the 2'-hydroxyl group by allowing an alkylating reagent to act on a ribonucleoside derivative represented by the following general formula (12).

[CHEMICAL 8]

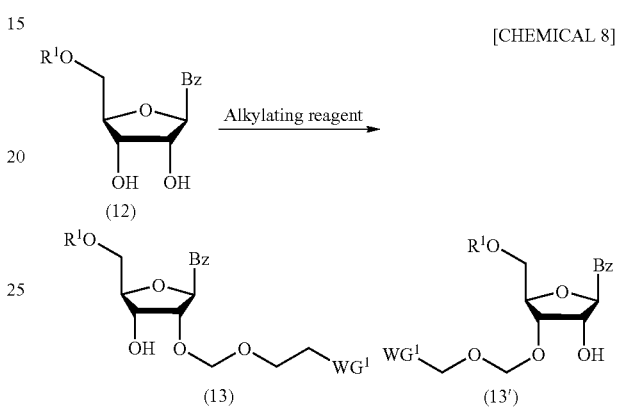

In the general formulae (12), (13) and (13'), $B_Z$, $R^1$ and $WG^1$ have the same meanings as above.

Examples of the "alkylating regent" may include an ether compound represented by the following general formula (14).

[CHEMICAL 9]

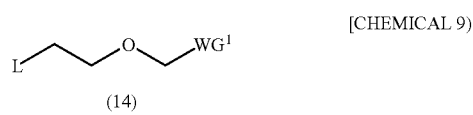

In the general formula (14), L represents halogen, an arylthio group, an alkyl sulfoxide group or an alkylthio group. $WG^1$ has the same meanings as above.

Examples of the "halogen", the "aryl" moiety of the "arylthio group", the "alkyl" moiety of the "alkylsulfoxide group" and the "alkylthio group" related to the L may include the same ones as those illustrated in the above description, respectively.

Specific examples of the ether compound (14) may include the following compounds 1 and 2:
1. chloromethyl 2-cyanoethyl ether
2. 2-cyanoethyl methylthiomethyl ether The ether compound (14) is a new alkylating reagent which can introduce an ether-type substituent, which is removable under neutral conditions, to the 2'-hydroxyl position under basic conditions, and which is useful as a reagent for producing the phosphoramidite compound (B).

The ether compound (14) can be produced by the following steps 1 to 4.

Step 1:

Process for producing a compound represented by the following general formula (16) by alkylthiomethylating an alcohol compound represented by the following general formula (15).

[CHEMICAL 10]

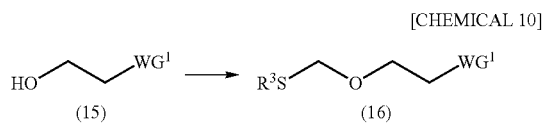

In the general formulae (15) and (16), $WG^1$ has the same meanings as above. $R^3$ represents alkyl or aryl.

The compound (16) is the ether compound (14), wherein L is an alkylthio group.

Examples of "alkyl" of $R^3$ may include the same ones as those illustrated for the "alkyl" related to the above-mentioned modified form of B.

When $R^3$ is methyl, examples of the "alkylthiomethylating reagent" may include a mixed solvent containing dimethylsulfoxide, acetic anhydride and acetic acid. The amount of dimethylsulfoxide to be used may be in the range of 10 to 200 mol per mol of compound (15), and preferably in the range of 20 to 100 mol per mol of the compound. The amount of acetic acid to be used may be in the range of 10 to 150 mol per mol of compound (15), and preferably in the range of 20 to 100 mol per mol of the compound. The amount of acetic anhydride to be used may be in the range of 10 to 150 mol per mol of compound (15), and preferably in the range of 20 to 100 mol per mol of the compound. The reaction temperature is preferably in the range of 0° C. to 100° C. The reaction time varies depending on the kind of raw materials and the reaction temperature, and is preferably between 1 and 48 hours.

Step 2:

Process for producing a compound represented by the following general formula (17) by halogenating compound (16).

[CHEMICAL 11]

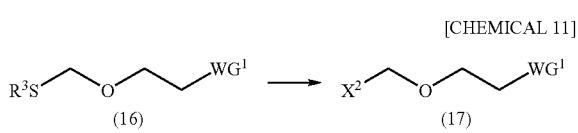

In the general formulae (16) and (17), $WG^1$ and $R^3$ have the same meanings as above. $X^2$ represents halogen.

Compound (17) is a compound wherein L of the ether compound (14) is halogen.

Examples of the "halogen" of $X^2$ may include the same ones as those illustrated for the "halogen" related to the above-mentioned modified form of B.

The step can be carried out by well-known methods (e.g., T. Benneche et al., Synthesis 762 (1983)). The solvent to be used is not specifically limited unless it is involved in the reaction, and may include, for example, a halogenated hydrocarbon such as methylene chloride, chloroform, carbon tetrachloride, 1,2-dichloroethane. Examples of the "halogenating reagent" may include sulfuryl chloride and phosphorus oxychloride. The amount of the halogenating reagent to be used may suitably be in the range of 0.8 to 20 mol per mol of compound (16), and preferably 1 to 10 mol per mol of the compound. The reaction temperature is preferably in the range of 0° C. to 100° C. The reaction time varies depending on the kind of raw materials and the reaction temperature, and is preferably between 30 minutes and 24 hours.

Step 3:

Process for producing a compound represented by the following general formula (18), by arylthiolating the compound (17).

[CHEMICAL 12]

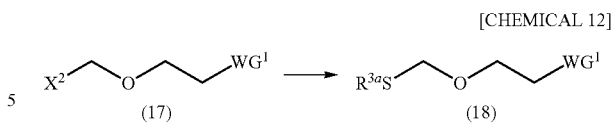

In the general formulae (17) and (18), $WG^1$ and $X^2$ have the same meanings as above. $R^{3a}$ represents aryl.

Compound (18) is a compound (14), wherein L is an arylthio group.

Examples of "aryl" of $R^{3a}$ may include the same ones as those illustrated for the "aryl" related to the above-mentioned modified form of B.

The step can be carried out by a known method. The solvent to be used is not specifically limited unless it is involved in the reaction, and may include, for example, methylene chloride and acetonitrile. Examples of the "arylthiolating reagent" may include thiophenol and 4-methylbenzenethiol. The amount of the arylthiolating reagent to be used may be in the range of 0.8 to 20 mol per mol of the compound (17), and preferably 1 to 5 mol per mol the compound. The reaction temperature is preferably in the range of 0° C. to 100° C. The reaction time varies depending on the kind of raw materials and the reaction temperature, and is preferably between 1 and 48 hours.

Step 4:

Process for producing a compound represented by the following general formula (19) by oxidizing the compound (16).

[CHEMICAL 13]

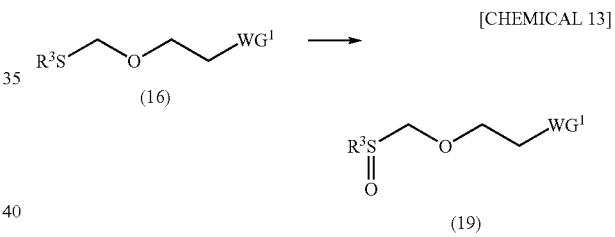

In the general formulae (16) and (19), $WG^1$ and $R^3$ have the same meanings as above.

The compound (19) is a compound (14), wherein L is an alkyl sulfoxide group.

Examples of the "alkyl" related to $R^3$ may include the same ones as those illustrated for the "alkyl" related to the above-mentioned modified form of B.

The step can be carried out by a known method. The solvent to be used is not specifically limited unless it is involved in the reaction, and may include, for example, methylene chloride, chloroform and methanol. Examples of the "oxidizing agent" may include m-chloroperbenzoic acid, metaperiodate salt and hydrogen peroxide. The amount of the oxidizing agent to be used may be in the range of 0.8 to 10 mol per of compound (16), and preferably 1 to 2 mol per mol of the compound. The reaction temperature is preferably in the range of 0° C. to 100° C. The reaction time varies depending on the kind of raw materials and the reaction temperature, and is preferably between 1 and 48 hours.

When compound (17) is used as the alkylating reagent, the step can be performed as follows.

The step can be performed by reacting the alkylating reagent and a base with ribonucleic acid derivative (12), which is commercially available or is synthesized according to a known method. The solvent to be used is not specifically limited unless it is involved in the reaction, and may include, for example, a halogenated hydrocarbon such as methylene chloride, chloroform, carbon tetrachloride and 1,2-dichloroethane. The amount of the alkylating reagent to be used may be in the range of 0.8 to 20 mol per mol of ribonucleic acid derivative (12), and preferably 1 to 10 mol per mol of the compound. In the step, the alkylating reagent may be reacted through the intermediate produced by reacting a metal reagent and a base with ribonucleic acid derivative (12), if necessary. Examples of the "metal reagent" may include dibutylstannyl dichloride. The amount of the metal reagent to be used may be in the range of 0.8 to 20 mol per mol of ribonucleic acid derivative (12), and preferably 1 to 10 mol per mol of the compound. Examples of the "base" may include an organic bases such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene. The amount of the base to be used may be in the range of 0.8 to 20 mol per mol of ribonucleic acid derivative (12), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours.

When compound (16) or (18) is used as the alkylating reagent, the step can be performed as follows.

The step can be performed according to a known method (e.g., M. Matteucci, Tetrahedron Letters, Vol. 31, 2385 (1990)) by reacting the alkylating reagent, an acid and a reagent for halogenating the sulfur atom on ribonucleic acid derivative (12) which is commercially available or is synthesized according to a known method. The amount of the alkylating reagent to be used may be in the range of 0.8 to 5 mol per mol of ribonucleic acid derivative (12), and preferably 1 to 3 mol per mol of the compound. Examples of the "acid" may include trifluoromethanesulfonic acid, silver trifluoromethanesulfonate and trimethylsilyl trifluoromethanesulfonate. The amount of the acid to be used may be in the range of 0.01 to 20 mol per mol of ribonucleic acid derivative (12), and preferably 0.02 to 10 mol per mol of the compound. The solvent to be used is not specifically limited unless it is involved in the reaction, and may include, for example, methylene chloride, chloroform, carbon tetrachloride, 1,2-dichloroethane, benzene, toluene, xylene, THF, acetonitrile and mixtures thereof. Examples of the "reagent for halogenating a sulfur atom" to be used in the step may include N-bromosuccinimide (NBS) and N-iodosuccinimide (NIS). The amount of the reagent for halogenating a sulfur atom to be used may be in the range of 0.8 to 10 mol per mol of ribonucleic acid derivative (12), and preferably 1 to 5 mol per mol of the compound. The reaction temperature is preferably in the range of −78° C. to 30° C. The reaction time varies depending on the kind of raw materials and the reaction temperature, and is preferably between 5 minutes and 5 hours.

When the compound (19) is used as the alkylating reagent, the step can be performed as follows.

The step can be performed by reacting the alkylating reagent, an acid anhydride and a base with ribonucleic acid derivative (12), which is commercially available or is synthesized according to a known method. The amount of the alkylating reagent to be used may be in the range of 0.8 to 5 mol per mol of ribonucleic acid derivative (12), and preferably 1 to 3 mol per mol of the compound. Examples of the "acid anhydride" may include trifluoromethanesulfonic anhydride and acetic anhydride. The amount of the acid anhydride to be used may be in the range of 0.01 to 20 mol per mol of ribonucleic acid derivative (12), and preferably 0.02 to 10 mol per mol of the compound. Examples of the "base" may include tetramethylurea and collidine. The amount of the base to be used may be in the range of 0.01 to 20 mol per mol of ribonucleic acid derivative (12), and preferably 0.02 to 10 mol per mol of the compound. The solvent to be used is not specifically limited unless it is involved in the reaction, and may include, for example, methylene chloride, chloroform, carbon tetrachloride, 1,2-dichloroethane and mixtures thereof. The reaction temperature is preferably in the range of −78° C. to 30° C. The reaction time varies depending on the kind of raw materials and the reaction temperature, and is preferably between 5 minutes and 24 hours.

(2) Step b:

Process for isolating and purifying the ribonucleoside derivative (13) produced by Step a;

In the step, the nucleoside derivative can be isolated and purified from the mixture produced by Step a by using a standard separation and purification technique such as thin-layer chromatography, silica gel column chromatography or the like.

(3) Step c:

Process for producing a ribonucleic acid derivative represented by the following general formula (21), wherein an ether-type protecting group which can be removed under neutral conditions is introduced to the 2'-hydroxyl group, by allowing an alkylating reagent to act on a ribonucleic acid derivative represented by the following general formula (20), being independent of Step b.

[CHEMICAL 14]

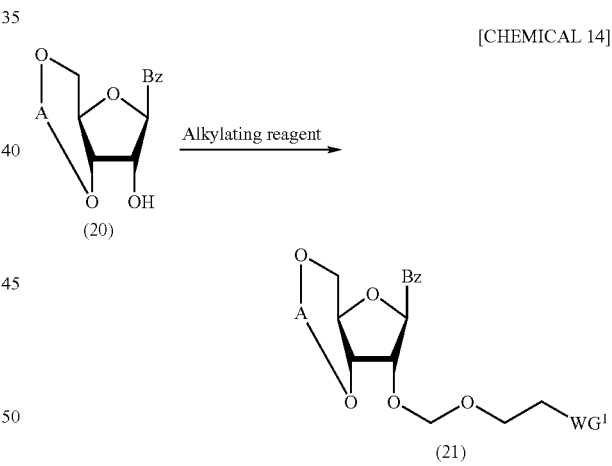

In the general formulae (20) and (21), $B_Z$ and $WG^1$ have the same meanings as above.

A represents a silicon substituent represented by the following general formulae (22a) or (22b).

[CHEMICAL 15]

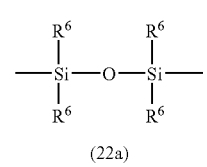

(22a)

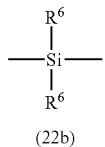

(22b)

In the general formulae (22a) and (22b), $R^6$ represents alkyl.

Examples of the "alkyl" of $R^6$ may include the same ones as those illustrated for the "alkyl" related to the above-mentioned modified form of B.

Examples of the "alkylating reagent" may include the same meanings as above.

When the compound (17) is used as the alkylating reagent, the step can be performed as follows.

The step can be performed by reacting the alkylating reagent and a base with ribonucleic acid derivative (20), which is commercially available or is synthesized according to a known method. The solvent to be used is not specifically limited unless it is involved in the reaction, and may include, for example, halogenated hydrocarbon such as methylene chloride, chloroform, carbon tetrachloride and 1,2-dichloroethane. The amount of the alkylating reagent to be used may be in the range of 0.8 to 20 mol per mol of ribonucleic acid derivative (20), and preferably 1 to 10 mol per mol of the compound. In the step, the alkylating reagent may be reacted through the intermediate produced by reacting a metal reagent and a base with ribonucleic acid derivative (20), if necessary. Examples of the "metal reagent" may include dibutylstannyl dichloride and tert-butylmagnesium chloride. The amount of the metal reagent to be used may be in the range of 0.8 to 20 mol per mol of ribonucleic acid derivative (20), and preferably 1 to 10 mol per mol of the compound. Examples of the "base" may include an organic bases such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene. The amount of the base to be used may be in the range of 0.8 to 20 mol per mol of ribonucleic acid derivative (20), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours.

When the compound (16) or (18a) is used as the alkylating reagent, the step can be performed as follows.

The step can be performed according to a known method (for example, M. Matteucci, Tetrahedron Letters, Vol. 31, 2385 (1990)) by reacting the alkylating reagent, an acid and a reagent for halogenating the sulfur atom on ribonucleic acid derivative (20), which is commercially available or is synthesized by a known method. The amount of the alkylating reagent to be used may be in the range of 0.8 to 5 mol per mol of ribonucleic acid derivative (20), and preferably 1 to 3 mol per mol of the compound. Examples of the "acid" may include trifluoromethanesulfonic acid, silver trifluoromethanesulfonate and trimethylsilyl trifluoromethanesulfonate. The amount of the acid to be used may be in the range of 0.01 to 20 mol per mol of ribonucleic acid derivative (20), and preferably 0.02 to 10 mol per mol of the compound. The solvent to be used is not specifically limited unless it is involved in the reaction, and may include, for example, methylene chloride, chloroform, carbon tetrachloride, 1,2-dichloroethane, benzene, toluene, xylene, THF, acetonitrile and mixtures thereof. Examples of the "reagent for halogenating a sulfur atom" to be used in the step may include N-bromosuccinimide (NBS) and N-iodosuccinimide (NIS). The amount of the reagent for halogenating a sulfur atom to be used may be in the range of 0.8 to 10 mol per mol of ribonucleic acid derivative (20), and preferably 1 to 5 mol per mol of the compound. The reaction temperature is preferably in the range of −78° C. to 30° C. The reaction time varies depending on the kind of raw materials and the reaction temperature, and is preferably between 5 minutes and 5 hours.

When the compound (19) is used as the alkylating reagent, the step can be performed as follows.

The step can be performed by reacting the alkylating reagent, an acid anhydride and base with ribonucleic acid derivative (20), which is commercially available or is synthesized according to a known method. The amount of the alkylating reagent to be used may be in the range of 0.8 to 5 mol per mol of ribonucleic acid derivative (20), and preferably 1 to 3 mol per mol of the compound. Examples of the "acid anhydride" may include trifluoromethanesulfonic anhydride and acetic anhydride. The amount of the acid anhydride to be used may be in the range of 0.01 to 20 mol per mol of ribonucleic acid derivative (20), and preferably 0.02 to 10 mol per mol of the compound. Examples of the "base" may include tetramethylurea and collidine. The amount of the base to be used may be in the range of 0.01 to 20 mol per mol of ribonucleic acid derivative (20), and preferably 0.02 to 10 mol per mol of the compound. The solvent to be used is not specifically limited unless it is involved in the reaction, and may include, for example, methylene chloride, chloroform, carbon tetrachloride, 1,2-dichloroethane and mixtures thereof. The reaction temperature is preferably in the range of −78° to 30° C. The reaction time varies depending on the kind of raw materials and the reaction temperature, and is preferably between 5 minutes and 24 hours.

(4) Step d:

Process for producing a ribonucleic acid derivative represented by the following general formula (23) by allowing dimethylsulfoxide, acetic acid and acetic anhydride to act on the ribonucleic acid derivative (20), being independent of Steps a to c.

[CHEMICAL 16]

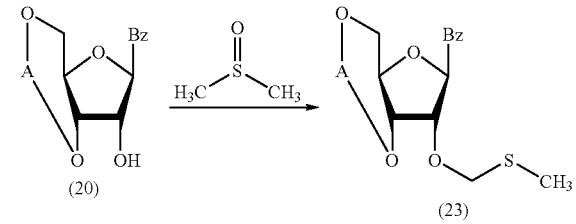

In the general formulae (20) and (23), A and $B_Z$ have the same meanings as above.

The step can be performed by reacting dimethylsulfoxide, acetic acid and acetic anhydride with ribonucleic acid derivative (20), which is commercially available or is synthesized according to a known method. The amount of the dimethylsulfoxide to be used may be in the range of 10 to 200 mol per mol of ribonucleic acid derivative (20), and preferably 20 to 100 mol per mol of the compound. The amount of the acetic acid to be used may be in the range of 10 to 150 mol per mol of ribonucleic acid derivative (20), and preferably 20 to 100 mol per mol of the compound. The amount of the acetic anhydride to be used may be in the range of 10 to 150 mol per mol of ribonucleic acid derivative (20), and preferably 20 to 100 mol per mol of the compound. The reaction temperature is preferably in the range of 10° C. to 50° C. The reaction time varies depending on the kind of raw materials and the reaction temperature, and is preferably between 30 minutes and 24 hours.

(5) Step e:

Process for producing a ribonucleic acid derivative represented by the following general formula (21), wherein an ether-type protecting group which can be removed under neutral conditions is introduced to the 2'-hydroxyl group, by allowing an alcohol compound represented by the following general formula (24), an acid and a reagent for halogenating a sulfur atom to act on a ribonucleic acid derivative (23) produced by Step d.

[CHEMICAL 17]

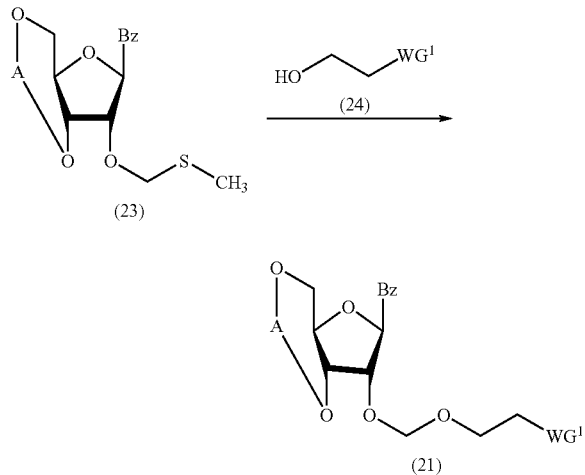

In the general formulae (21), (23) and (24), A, $B_Z$ and $WG^1$ have the same meanings as above.

The step can be performed by reacting the alcohol compound (24), an acid and a reagent for halogenating the sulfur atom on the ribonucleic acid derivative (23) according to a known method. The solvent to be used is not specifically limited unless it is involved in the reaction, and may include, for example, methylene chloride, chloroform, carbon tetrachloride, 1,2-dichloroethane, benzene, toluene, xylene, THF, acetonitrile and mixtures thereof. The amount of the alcohol compound (24) to be used may be in the range of 0.8 to 20 mol per mol of ribonucleic acid derivative (23), and preferably 1 to 10 mol per mol of the compound. Examples of the "acid" may include trifluoromethanesulfonic acid, silver trifluoromethanesulfonate and trimethylsilyl trifluoromethanesulfonate. Examples of the "reagent for halogenating a sulfur atom" may include N-bromosuccinimide (NBS) and N-iodosuccinimide (NIS). The amount of the reagent for halogenating a sulfur atom to be used may be in the range of 0.1 to 20 mol per mol of ribonucleic acid derivative (23), and preferably 0.2 to 10 mol per mol of the compound. The reaction temperature is preferably in the range of −100° C. to 20° C. The reaction time varies depending on the kind of raw materials and the reaction temperature, and is preferably between 5 minutes and 12 hours.

(6) Step f:

Process for producing a ribonucleic acid derivative represented by the following general formula (25) by removing the protecting group of the 3'- and 5'-hydroxyl groups of the ribonucleic acid derivative (21) produced by Step c or e.

[CHEMICAL 18]

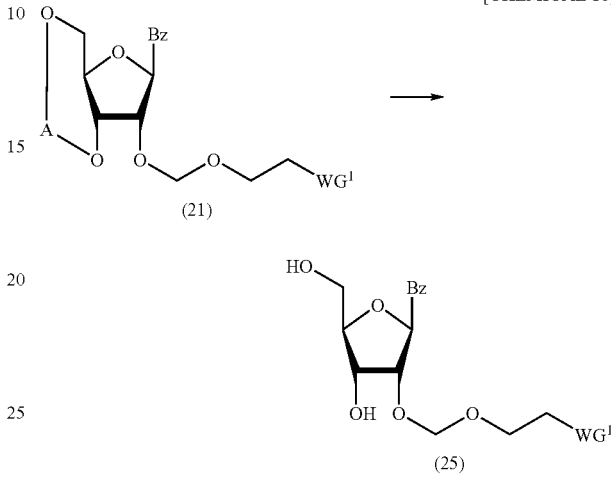

In the general formulae (21) and (25), A, $B_Z$ and $WG^1$ have the same meanings as above.

The step can be performed by dissolving the ribonucleic acid derivative (21) in an organic solvent, and reacting a fluorinating agent alone or a mixture of a fluorinating agent and an acid (e.g., acetic acid, hydrochloric acid, sulfuric acid) in an arbitrary mixing ratio. Examples of the "fluorinating agent" to be used in the step may include ammonium fluoride, TBAF, triethylamine trihydrofluoride and hydrogen fluoride pyridine. The amount of the fluorinating agent to be used may be in the range of 0.1 to 20 mol per mol of ribonucleic acid derivative (21), and preferably 0.2 to 10 mol per mol of the compound. The reaction temperature is preferably in the range of 0° C. to 120° C. The reaction time varies depending on the kind of raw materials and the reaction temperature, and is preferably between 30 minutes and 24 hours.

The ratio of the fluorinating agent and the acid in the mixed reagent may be in the range of 1:0.1 to 1:2, and preferably 1:1 to 1:1.2.

(7) Step g:

Process for producing a ribonucleic acid derivative (13) by introducing a protecting group ($R^1$), which can be removed under acidic conditions, into the 5'-hydroxyl group of the ribonucleic acid derivative (25) produced by step f.

[CHEMICAL 19]

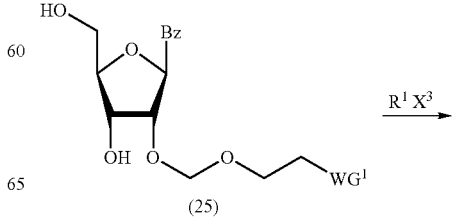

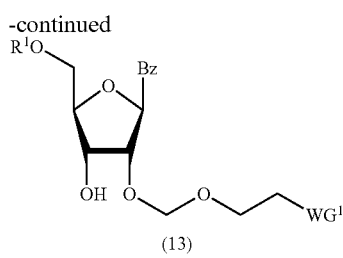

(13)

In the general formulae (13) and (25), $B_z$, $R^1$ and $WG^1$ have the same meanings as above. $X^3$ represents halogen.

Examples of the "halogen" of $X^3$ may include the same ones as those illustrated for the "halogen" related to the above-mentioned modified form of B.

The step can be performed by reacting $R^1X^3$ with a ribonucleic acid derivative (25) according to a known method. The amount of $R^1X^3$ to be used may be in the range of 0.8 to 20 mol per mol of ribonucleic acid derivative (25), and preferably 1 to 10 mol per mol of the compound. The solvent to be used is not specifically limited unless it is involved in the reaction, and may include, for example, acetonitrile and THF. Examples of the "base" may include an organic base such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene. The amount of the base to be used may be in the range of 0.8 to 20 mol per mol of ribonucleic acid derivative (25), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours.

(8) Step h:

Process for producing the phosphoramidite compound (B), wherein 3'-hydroxyl group is phosphoramidited, by allowing a phosphoramiditing reagent and an activating agent, if necessary, to act on a ribonucleic acid derivative (13) produced by step b or step f.

[CHEMICAL 20]

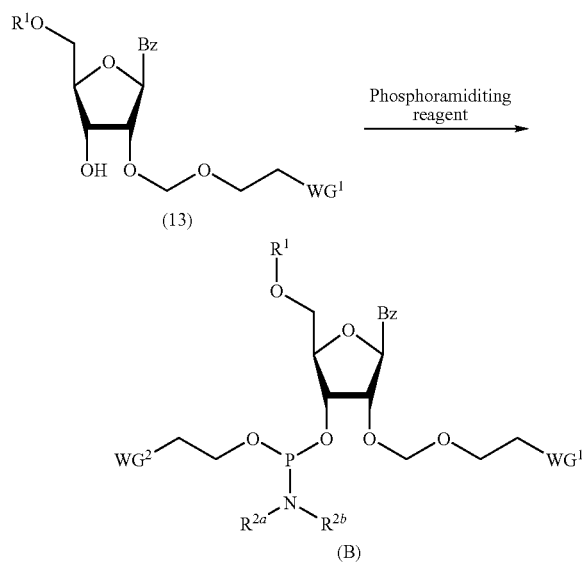

In the general formulae (13) and (B), $B_z$, $R^1$, $R^{2a}$, $R^{2b}$, $WG^1$ and $WG^2$ have the same meanings as above.

Examples of the "phosphoramiditing reagent" may include a compound represented by the following general formulae (26a) and (26b).

[CHEMICAL 21]

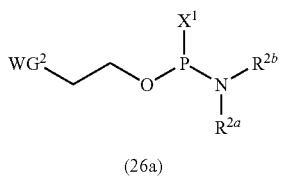

(26a)

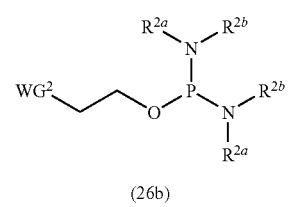

(26b)

In the general formulae (26a) and (26b), $R^{2a}$, $R^{2b}$ and $WG^2$ have the same meanings as above. $X^1$ represents halogen.

Examples of the "halogen" may include the same ones as those illustrated for the "halogen" related to the above-mentioned modified form of B.

The step is a reaction for phosphoramiditing the 3'-hydroxyl group by reacting the phosphoramiditing reagent with a ribonucleic acid derivative (13), and can be performed according to a known method. An activating agent can be used if necessary. The solvent to be used is not specifically limited unless it is involved in the reaction, and may include, for example, acetonitrile and THF. The amount of the phosphoramiditing reagent to be used may be in the range of 0.8 to 20 mol per mol of ribonucleic acid derivative (13), and preferably 1 to 10 mol per mol of the compound. Examples of the "activating agent" may include 1H-tetrazole, 5-ethylthiotetrazole, 5-benzylmercapto-1H-tetrazole, 4,5-dichloroimidazole, 4,5-dicyanoimidazole, benzotriazole triflate, imidazole triflate, pyridinium triflate, N,N-diisopropylethylamine and 2,4,6-collidine/N-methylimidazole. The amount of the activating agent to be used may be in the range of 0.8 to 20 mol per mol of ribonucleic acid derivative (13), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours. The phosphoramidite compound (B) thus produced can be isolated and purified by a method known per se, such as concentration, liquid phase conversion, partition, solvent extraction, crystallization, recrystallization, fractional distillation or chromatography.

III. A Method for Producing the Oligo-RNA (A)

The details are described below about a method for producing the oligo-RNA (A).

[CHEMICAL 22]

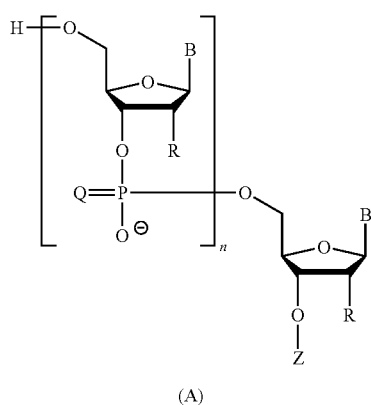

(A)

In the general formula (A), each B, each Q and each R have independently the same meanings as above. n and Z have the same meanings as above.

A method for producing oligo-RNA (A) can be performed by a known method, for example, by condensing a nucleic acid monomer compound to the direction from 3' to 5' step by step according to the following steps A to H.

Compounds and reagents to be used in the following step except the phosphoramidite compound (B) are not particularly limited as long as they are generally used in synthesis of oligo-RNAs or oligo-DNAs. In addition, all the steps can be performed by using an automatic synthesizer for DNA or in manual as in the case of using conventional agents for synthesizing a nucleic acid. The use of an automatic synthesizer is desirable from the point of view of the simplicity and ease of the method and the accuracy of the synthesis. Compounds and reagents described in the following steps A to G except a nucleic acid monomer compound are not particularly limited as long as they are generally used in synthesis of oligo-DNAs or oligo-RNAs.

Compounds and reagents to be used except a nucleic acid monomer compound described in the following step A to step H are not particularly limited as long as they are generally used in synthesis of oligo-RNAs or oligo-DNAs.

Additionally, in the method for producing the oligo-RNA (A), an oligo-RNA (A) of which at least one R is hydroxyl group can be produced by using at least once the phosphoramidite compound (B) as a nucleic acid monomer compound.

Furthermore, in step B mentioned below, an oligo-RNA (A) in which all Rs are hydroxyl group can be produced by invariably using the phosphoramidite compound (B) as a nucleic acid monomer compound.

(1) Step A:

Process for producing an (oligo)nucleic acid derivative represented by the following general formula (2) by removing the 5'-hydroxyl group from an (oligo) nucleic acid derivative represented by the following general formula (1) by allowing an acid to act on it.

[CHEMICAL 23]

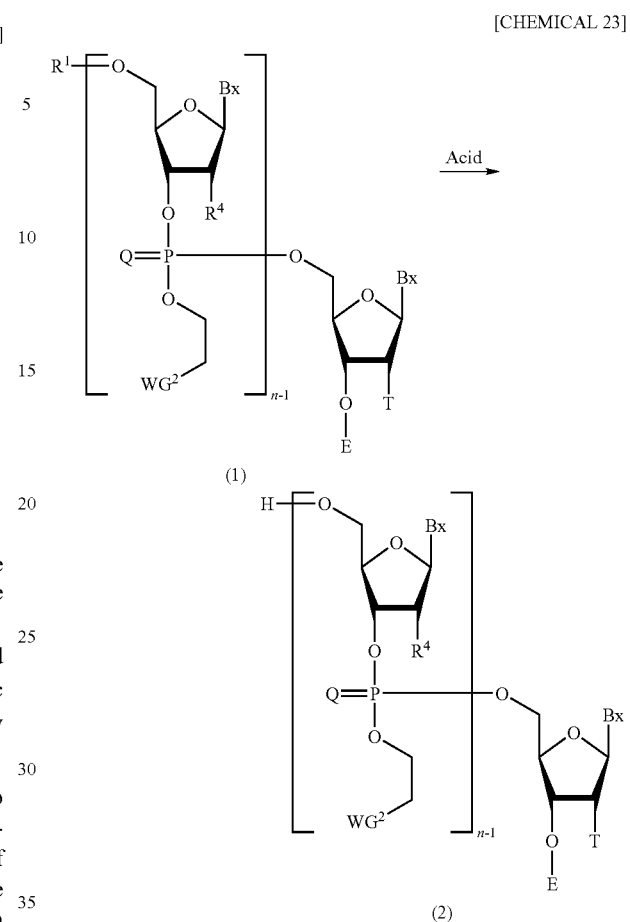

In the general formulae (1) and (2), n and $R^1$ have the same meanings as above. Each Q, each $R^4$ and each $WG^2$ independently have the same meanings as above. Each $B_X$ independently represents a nucleobase or a modified form thereof. E represents acyl or a substituent represented by the following general formula (5).

[CHEMICAL 24]

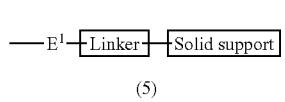

(5)

In the general formula (5), $E^1$ represents single bond or a substituent represented by the following general formula (6).

[CHEMICAL 25]

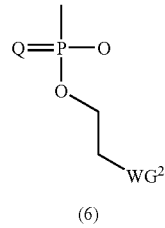

(6)

In the general formula (6), Q and $WG^2$ have the same meanings as above.

T represents H, acyloxy, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy and a substituent represented by the above-mentioned general formula (4) or a substituent represented by the following general formula (5), with the proviso that either E or T is a substituent (5).

The "nucleobase" represented by $B_X$ is not particularly limited as long as it is a nucleobase to be used in the synthesis of a nucleic acid, and examples thereof may include pyrimidine bases such as cytosine, uracil and thymine, purine bases such as adenine and guanine. The "nucleobase" of $B_X$ may be protected, and particularly in the case of a nucleobase having an amino group such as adenine, guanine or cytosine, the amino group thereof is preferably protected. The "protecting group for the amino group" is not particularly limited as long as it is a protecting group used as a protecting group for a nucleic acid, and may include, for example, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene.

The "modified form" of $B_X$ is the group in which a nucleobase has been substituted by an arbitrary substituent.

Examples of "substituent" related to the "modified form" of $B_X$ may include halogen, acyl, alkyl, arylalkyl, alkoxy, alkoxyalkyl, hydroxyl, amino, monoalkylamino, dialkylamino, carboxy, cyano and nitro. The modified form of $B_X$ may be substituted by 1 to 3 of these substituents at arbitrary positions.

Examples of the "halogen", "acyl", "alkyl", "arylalkyl", "alkoxy", "alkoxyalkyl", "monoalkylamino" and "dialkylamino" related to the modified form of $B_X$ may include the same ones as those related to the above-mentioned modified form of B.

Examples of the "acyl" related to the E may include the same ones as those illustrated for the "acyl" related to the above-mentioned modified form of B.

Examples of the "acyl" moiety of "acyloxy" related to the T may include the same ones as those illustrated for the "acyl" related to the above-mentioned modified form of B.

Examples of the "halogen", "alkoxy", "alkylamino" and "dialkylamino" related to the T may include the same ones as those illustrated in the above description, respectively.

Examples of the "alkyl" moiety of "alkoxyalkyloxy" and "alkylthio" related to the T may include the same ones as those illustrated for the "alkyl" related to the above-mentioned modified form of B.

Examples of the "alkoxy" moiety of "alkoxyalkyloxy" related to the T may include the same ones as those illustrated for the "alkoxy" related to the above-mentioned modified form of B.

Examples of the "alkenyl" moiety of "alkenyloxy", "alkenylthio", "alkenylamino", "dialkenylamino" related to the T may include the same ones as those illustrated for the "alkenyl" related to the above-mentioned R.

Examples of the "alkynyl" moiety of "alkynyloxy", "alkynylthio", "alkynylamino", "dialkynylamino" related to the T may include the same ones as those illustrated for the "alkynyl" related to the above-mentioned R.

The "alkylamino", "alkenylamino" and "alkynylamino" related to the T may be protected, and the protecting group of the amino group is not particularly limited as long as it is a protecting group to be used as an amino group, and specific examples thereof may include trifluoroacetyl, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene. Particularly, trifluoroacetyl is preferred.

The step is performed by reacting an acid to a compound represented by the following formula (27a), (27b) (a nucleic acid derivative (1), wherein n is 1) which is attached to the solid support, or an oligo-RNA or an oligo-DNA produced by performing the operations of step A to step D (oligonucleic acid derivative (1), wherein n is 2 to 100) which is attached to the solid support (hereinafter referred to as the "compound attached the solid support").

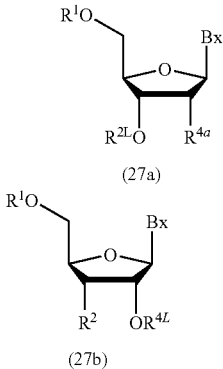

[CHEMICAL 26]

In the general formulae (27a) and (27b), $B_X$ and $R^1$ have the same meanings as above. $R^{2L}$ and $R^{4L}$ represent the substituent (5). $R^2$ represents acyloxy. $R^{4a}$ represents H, acyloxy, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or the substituent (4).

Examples of "acyl" moiety of the "acyloxy" related to $R^2$ and $R^{4a}$ may include the same ones as those illustrated for the "acyl" related to the above-mentioned modified form of B.

Examples of the "halogen", "alkoxy", "alkylamino" and "dialkylamino" related to $R^{4a}$ may include the same ones as those illustrated in the above description, respectively.

Examples of the "alkyl" moiety of "alkoxyalkyloxy" and "alkylthio" related to $R^{4a}$ may include the same ones as those illustrated for the "alkyl" related to the above-mentioned modified form of B.

Examples of the "alkoxy" moiety of "alkoxyalkyloxy" related to $R^{4a}$ may include the same ones as those illustrated for the "alkoxy" related to the above-mentioned modified form of B.

Examples of the "alkenyl" moiety of "alkenyloxy", "alkenylthio", "alkenylamino" and "dialkenylamino" related to $R^{4a}$ may include the same ones as those illustrated for the "alkenyl" related to the above-mentioned R.

Examples of the "alkynyl" moiety of "alkynyloxy", "alkynylthio", "alkynylamino" and "dialkynylamino" related to $R^{4a}$ may include the same ones as those illustrated for the "alkynyl" related to the above-mentioned R.

The "alkylamino", "alkenylamino" and "alkynylamino" related to $R^{4a}$ may be protected, and the "protecting group of the amino group" is not particularly limited as long as it is a protecting group to be used as a protecting group of an amino group, and specific examples thereof may include trifluoroacetyl, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene. Particularly, trifluoroacetyl is preferred.

Examples of the "solid support" may include a controlled-pore glass (CPG), an oxalyl-controlled pore glass (see, for example, Alul et al., Nucleic Acids Research, Vol. 19, 1527 (1991)), TentaGel support-amino polyethylene glycol derivatization support (see, for example, Wright et al., Tetrahedron Letters, Vol. 34, 3373 (1993)) and a copolymer of porous polystyrene and divinylbenzene.

Examples of the "linker" may include 3-aminopropyl, succinyl, 2,2'-diethanol sulfonyl and a long chain alkylamino (LCAA). The nucleic acid derivative (27a), the nucleic acid derivative (27b) are attached to the solid support, which are produced according to a known method or are commercially available, and examples of a preferable embodiment are a nucleic acid derivative represented by the following general formulae (28) and (29).

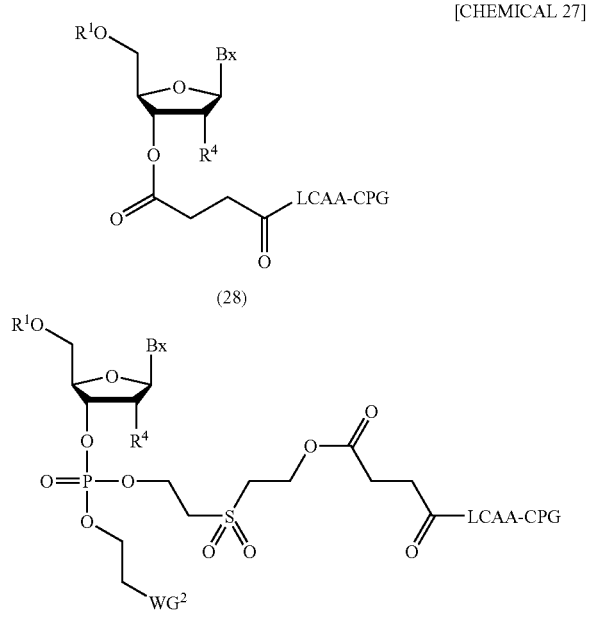

[CHEMICAL 27]

(28)

(29)

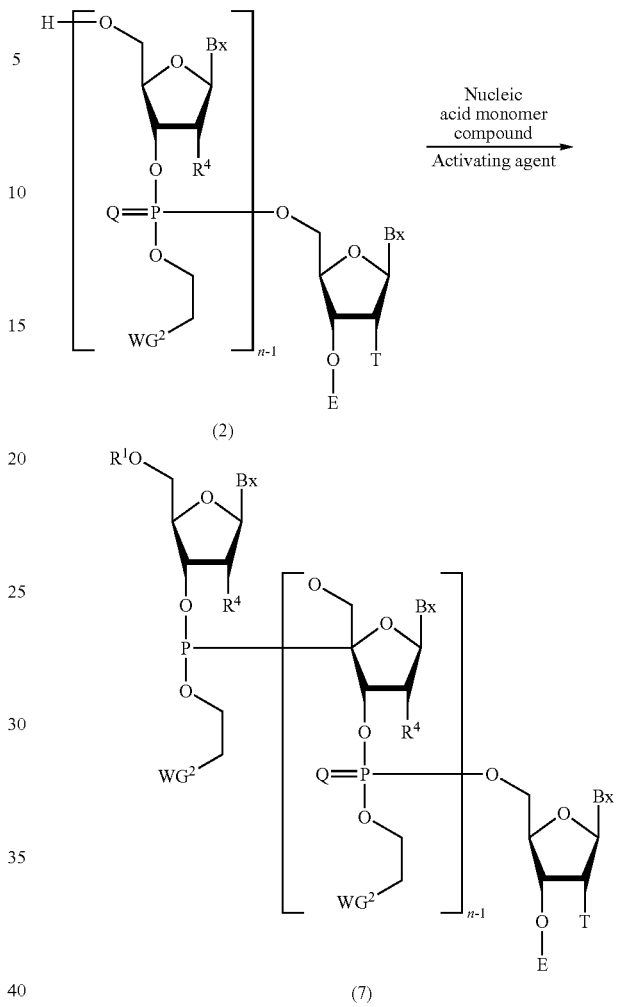

[CHEMICAL 28]

(2)

(7)

In the general formulae (28) and (29), $B_X$, Q, $R^1$, $R^4$ and $WG^2$ have the same meanings as above.

The nucleic acid derivative (28) and (29) wherein $R^4$ is a substituent (4) can be produced from a phosphoramidite compound (B) according to a known method.

Examples of the "acid" to be used in the step may include trifluoroacetic acid, dichloroacetic acid, and trichloroacetic acid.

The acid to be used in the step can be diluted in a suitable solvent so as to be of a concentration of 1 to 5%. The solvent is not specifically limited unless it is involved in the reaction, and may include dichloromethane, acetonitrile, water and an arbitrary mixture thereof. The reaction temperature of the reaction is preferably in the range of 20° C. to 50° C. The reaction time varies depending on the kind of the oligonucleic acid derivative (1), the acid and the reaction temperature, and is preferably between 1 minute and 1 hour. The amount of the reagent to be used is preferably in the range of 0.8 to 100 mol per mol of the (oligo)nucleic acid derivative attached to the solid phase support, and more preferably 1 to 10 mol per mol of the compound attached to the solid support.

(2) Step B:

Process for producing an oligonucleic acid derivative represented by the following general formula (7) by condensing a nucleic acid monomer compound with the (oligo) nucleic acid derivative (2) produced by Step A using an activating agent.

In the general formulae (2) and (7), each $B_X$, each Q, each $R^4$ and each $WG^2$ independently have the same meanings as above. E, n, $R^1$ and T have the same meanings as above.

The step can be performed by reacting a nucleic acid monomer compound and an activating agent with an oligonucleic acid derivative attached to the solid phase support.

Examples of the "nucleic acid monomer compound" may include the phosphoramidite compound (B) and a nucleic acid derivative represented by the following general formula (30).

[CHEMICAL 29]

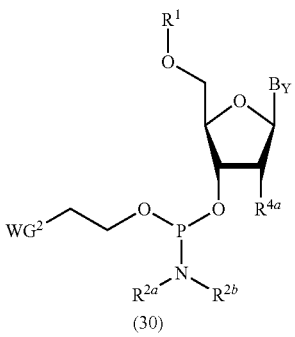

(30)

In the general formula (30), $R^1$, $R^{2a}$, $R^{2b}$, $R^{4a}$ and $WG^2$ have the same meanings as above. $B_Y$ represents a nucleobase which may have a protecting group or a modified form thereof.

The "nucleobase" related to $B_Y$ is not particularly limited as long as it is a nucleobase to be used in the synthesis of a nucleic acid, and may include pyrimidine bases such as cytosine, uracil and thymine, purine bases such as adenine and guanine. The "nucleobase" related to $B_Y$ may be protected, and particularly in the case of a nucleobase having an amino group such as adenine, guanine and cytosine, the amino group thereof is preferred to be protected. The "protecting group of the amino group" is not particularly limited as long as it is a protecting group to be used as a protecting group of a nucleic acid, and specific examples thereof may include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene.

A "modified form" of $B_Y$ is the group in which a nucleobase has been substituted by an arbitrary substituent. Examples of "substituent" related to the "modified form" of $B_Y$ may include halogen, acyl, alkyl, arylalkyl, alkoxy, alkoxyalkyl, hydroxyl, amino, monoalkylamino, dialkylamino, carboxy, cyano and nitro. The modified form of $B_Y$ may be substituted by 1 to 3 of these substituents at arbitrary positions.

Examples of the "halogen", "acyl", "alkyl", "arylalkyl", "alkoxy", "alkoxyalkyl", "monoalkylamino" and "dialkylamino" related to the modified form of $B_Y$ may include the same ones as those related to the above-mentioned modified form of B.

Examples of the "activating agent" may include the same meanings as above.

The reaction solvent to be used is not specifically limited unless it is involved in the reaction, and may include, for example, acetonitrile and THF. The reaction temperature in the reaction is preferably in the range of 20° C. to 50° C. The reaction temperature varies depending on the kind of the oligonucleic acid derivative (2), the kind of an activating agent to use and the reaction temperature, and preferably between 1 minute and 1 hour. The amount of the agent to be used is preferably in the range of 0.8-100 mol per mol of the oligonucleic acid derivative attached to the solid phase support, and more preferably 1 to 10 mol per mol of the compound attached to the solid support.

(3) Step C:

Process for capping the 5'-hydroxyl group of the unreacted (oligo)nucleic acid derivative (2) in step B.

[CHEMICAL 30]

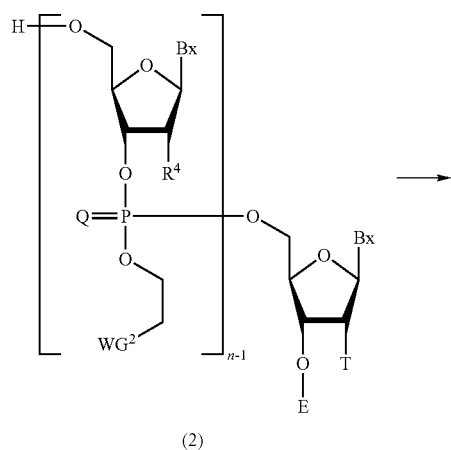

(2)

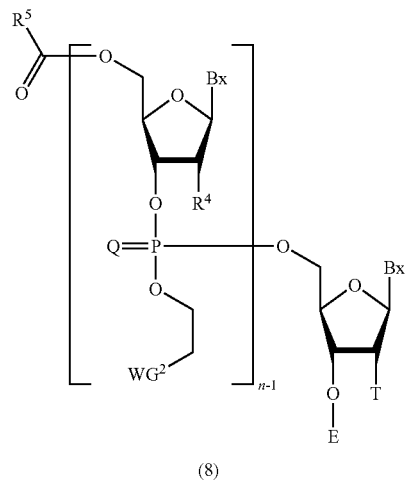

(8)

In the general formulae (2) and (8), each $B_X$, each Q, each $R^4$, each $WG^2$ independently have the same meanings as above. E, n and T have the same meanings as above. $R^5$ represents methyl, phenoxymethyl and tert-butylphenoxymethyl.

The step is a reaction for protecting the 5'-hydroxyl group unreacted in step B, and can be performed by reacting a capping agent with an oligonucleic acid derivative attached to the solid phase support.

Examples of the "capping agent" may include acetic anhydride, phenoxyacetic anhydride and tert-butylphenoxyacetic anhydride. The capping agent to be used can be diluted in a suitable solvent so as to be of a concentration of 0.05 to 1 M. The reaction solvent to be used is not specifically limited unless it is involved in the reaction, and may include, for example, pyridine, methylene chloride, acetonitrile, THF and mixtures thereof. In addition, for example, 4-dimethylaminopyridine and N-methylimidazole can be used as a "reaction accelerator" in the step, if necessary. The reaction temperature in the reaction is preferably in the range of 20° C. to 50° C. The reaction time varies depending on the kind of the oligonucleic acid derivative (2), the capping agent and the reaction temperature, and is preferably between 1 and 30 minutes. The amount of the capping agent to be used is preferably in the range of 0.8-100 mol per mol of the oligonucleic acid derivative attached to the solid phase support, and more preferably 1 to 10 mol per mol of the compound attached to the solid support.

(4) Step D:

Process for converting a phosphite group into a phosphate group or a thiophosphate group by reacting the oligonucleic acid derivative (7) produced in Step B with an oxidizing agent.

[CHEMICAL 31]

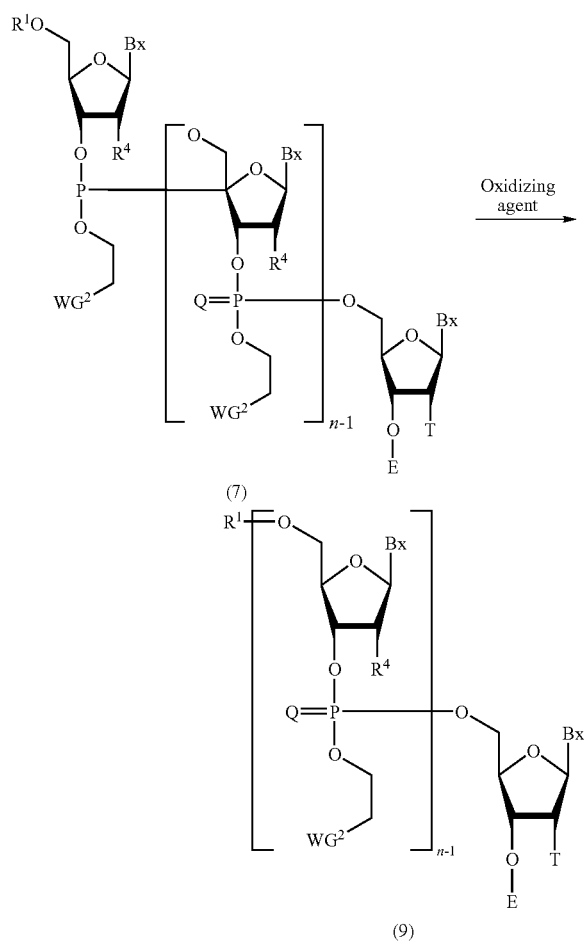

In the general formulae (7) and (9), each $B_x$, each Q, each $R^4$ and each $WG^2$ independently have the same meanings as above. E, n, $R^1$ and T have the same meanings as above.

The step is a reaction for converting trivalent phosphorus to pentavalent phosphorus by using an oxidizing agent, and can be performed by reacting an oxidizing agent with an oligonucleic acid derivative attached to the solid phase support.

When phosphorus is oxidized by oxygen, examples of the "oxidizing agent" may include iodine and tert-butylhydroperoxide. In addition, the oxidizing agent to be used can be diluted in a suitable solvent so as to be of a concentration of 0.05 to 2 M. The reaction solvent to be used is not specifically limited unless it is involved in the reaction, and may include, for example, pyridine, THF, water and mixtures thereof. For example, iodine/water/pyridine—THF, iodine/pyridine—acetic acid and a peroxidation agent (tert-butylhydroperoxide/methylene chloride and the like) can be used.

In addition, when phosphorus is oxidized by sulfur, examples of the "oxidizing agent" may include sulfur, Beaucage reagent (3H-1,2-benzodithiol-3-on-1,1-dioxide) and 3-amino-1,2,4-dithiazole-5-thione (ADTT). The oxidizing agent to be used can be diluted in a suitable solvent so as to be of a concentration of 0.01 to 2 M. The reaction solvent to be used is not specifically limited unless it is involved in the reaction, and may include, for example, methylene chloride, acetonitrile, pyridine and mixtures thereof. The reaction temperature is preferably in the range of 20° C. to 50° C. The reaction time varies depending on the kind of the oligonucleic acid derivative (7), the oxidizing agent and the reaction temperature, and is preferably between 1 and 30 minutes. The amount of the oxidizing agent to be used is preferably in the range of 0.8-100 mol per mol of the oligonucleic acid derivative attached to the solid phase support, and more preferably 1 to 50 mol per mol of the compound attached to the solid support.

(5) Step E:

Process for cleaving the oligonucleic acid derivative (9) produced by step D from the solid support, and then removing the protecting groups of each nucleobase and each phosphate group.

[CHEMICAL 32]

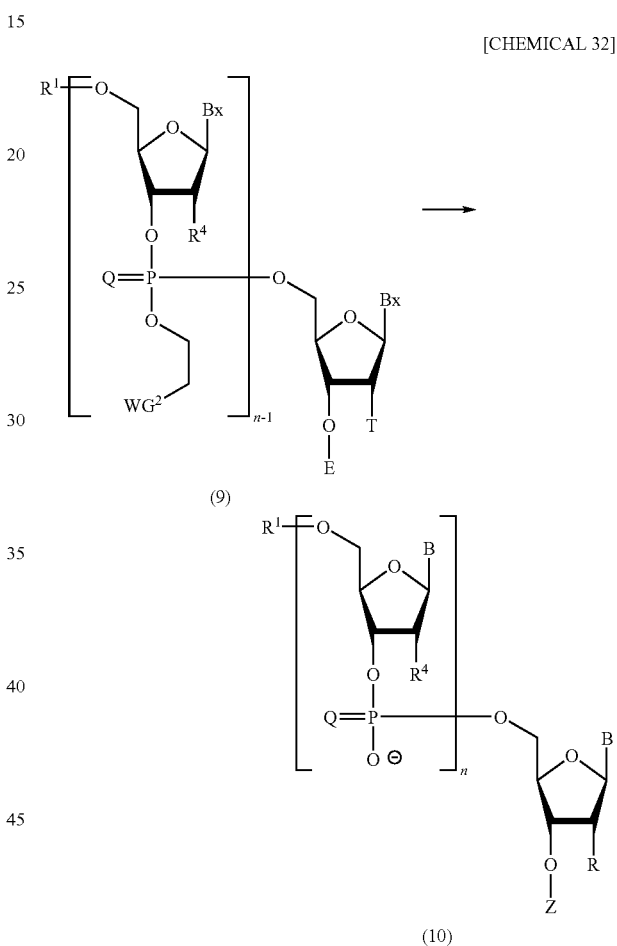

In the general formulae (9) and (10), each B, each $B_x$, each Q, each $R^4$ and each $WG^2$ independently have the same meanings as above. E, n, R, $R^1$, T and Z have the same meanings as above.

The cleaving step is a reaction for cleaving an oligo-RNA having a desired chain length from solid phase support and linker with a cleaving agent, and is performed by adding a cleaving agent to the solid support which contains an oligonucleic acid derivative having a desired chain length. In the step, the protecting group of a nucleobase can be removed.

Examples of the "cleaving agent" may include concentrated aqueous ammonia and methylamine. The cleaving agent to be used in the step may be diluted by, for example, water, methanol, ethanol, isopropyl alcohol, acetonitrile, THF and mixtures thereof. Among them, ethanol is preferred. The reaction temperature may be in the range of 15° C. to 75°

C., preferably it is 15° C. to 30° C., and more preferably reaction temperature is 18° C. to 25° C. The reaction time for deprotection varies depending on the kind of the oligonucleic acid derivative (9), the oxidizing agent and the reaction temperature, and may be in the range of 10 minutes to 30 hours, preferably 30 minutes to 24 hours, and more preferably 1 to 4 hours. The concentration of ammonium hydroxide in the solution to be used for deprotection may be 20 to 30% by weight, preferably 25 to 30% by weight, and preferably 28 to 30 by weight. The amount of the ammonium hydroxide to be used may be in the range of 1 to 100 mol per mol of the oligonucleic acid derivative attached to the solid phase support, and preferably 10 to 50 mol per mol of the compound attached to the solid support.

(6) Step F:

Process for producing an oligonucleic acid derivative represented by the following general formula (11), characterized by using a sulfoxide-based solvent or an amide-based solvent or a mixture thereof, each of which may contain THF, as a reaction solvent in the step of removing an ether-type protecting group, which protects the 2'-hydroxyl group of each ribose of an oligonucleic acid derivative represented by the following general formula (10) by allowing TBAF to act on the oligonucleic acid derivative.

[CHEMICAL 33]

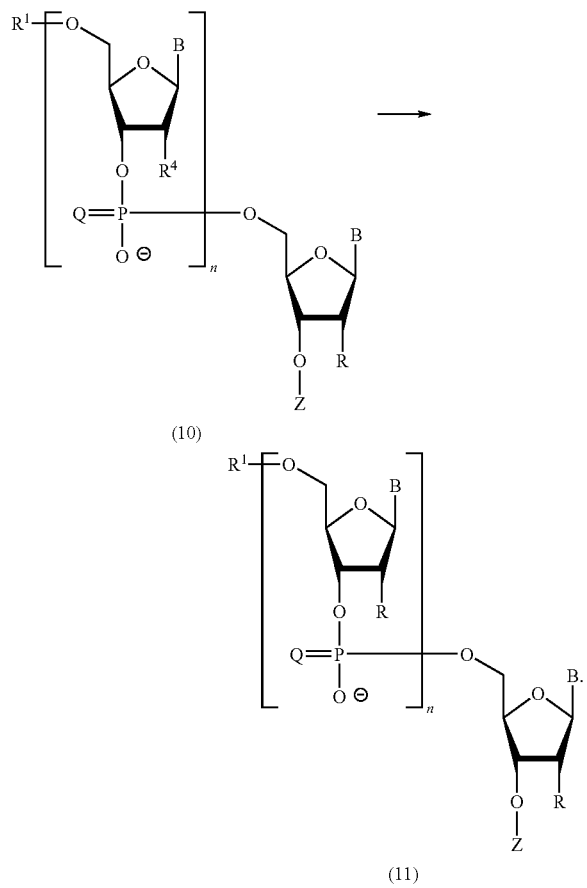

In the general formulae (10) and (11), each B, each Q, each R and each $R^4$ independently have the same meanings as above. n, and Z have the same meanings as above.

The step can be performed by reacting TBAF to the oligonucleic acid derivative (10). The amount of TBAF to be used may be in the range of 1 to 500 mol per mol of protecting group to be removed, and preferably 5 to 10 mol per mol of protecting group to be removed. The solvent to be used may include a sulfoxide-based solvent, an amide-based solvent or a mixture thereof, each of which may contain THF. In addition, when a sulfoxide-based solvent or amide-based solvent or a mixture thereof is used as a mixed solvent with THF, the amount of THF to be used is in the range of 0 to 95% by weight of a sulfoxide-based solvent or amide-based solvent or mixture thereof, and is preferably 0 to 50% by weight of a sulfoxide-based solvent or amide-based solvent or mixture thereof. The amount of "A sulfoxide-based solvent, an amide-based solvent or a mixture thereof, each of which may contain THF (the reaction solvent)" to be used varies depending on the kind of the oligonucleic acid derivative (10) and the reaction solvent to be used, and may be in the range of 0.8 to 100 mol per mol of TBAF, and preferably 1 to 10 mol per mol of TBAF. The reaction temperature varies depending on the kind of the oligonucleic acid derivative (10) and the reaction solvent to be used, and is preferably in the range of 20° C. to 80° C. The reaction time varies depending on the kind of the oligonucleic acid derivative (10), the reaction solvent and the reaction temperature, and is preferably in the range of 1 hour to 100 hours.

In addition, nitroalkane, alkylamine, amidine, thiol, thiol derivative and mixture thereof can be added as a scavenger of acrylonitrile, if necessary, to trap the acrylonitrile which is a by-product in the step. Examples of the "nitroalkane" may include straight nitroalkane having 1 to 6 carbon atoms. Specifically, the nitroalkane may include, for example, nitromethane. Examples of the "alkylamine" may include straight alkylamine having 1 to 6 carbon atoms. Specifically, the "alkylamine" may include, for example, methylamine, ethylamine, n-propylamine, n-butylamine, n-pentylamine and n-hexylamine. Examples of the "amidine" may include benzamidine and formamidine.

Examples of the "thiol" may include straight thiol having 1 to 6 carbon atoms. Specifically, the "thiol" may include, for example, methanethiol, ethanethiol, 1-propanethiol, 1-butanthiol, 1-pentanethiol and 1-hexanthiol. Examples of the "thiol derivative" may include alcohol and ether having the same or different straight alkylthiol having 1 to 6 carbon atoms. Specifically, the thiol derivative may include, for example, 2-mercaptoethanol, 4-mercapto-1-butanol, 6-mercapto-1-hexanol, mercaptomethyl ether, 2-mercaptoethyl ether, 3-mercaptopropyl ether, 4-mercaptobutyl ether, 5-mercaptopentyl ether and 6-mercaptohexyl ether.

The amount of the scavenger of acrylonitrile to be used varies depending on the kind of the oligonucleic acid derivative (10), and may be in the range of 0.1 to 500 mol per mol of 2-cyanoethoxymethyl substituting the 2'-hydroxyl group of each ribose of the oligonucleic acid derivative (10), and preferably 1 to 10 mol per mol.

(7) Step G:

Process for removing the 5'-hydroxyl group of the oligonucleic acid derivative (11).

[CHEMICAL 34]

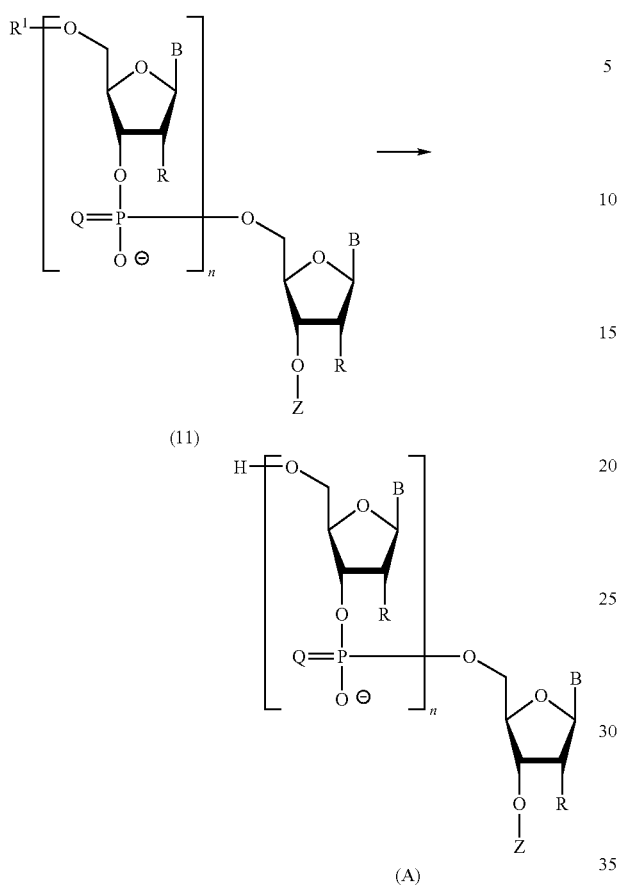

In the general formulae (11) and (A), each B, each Q and each R independently have the same meanings as above. n, $R^1$ and Z have the same meanings as above.

The step is a reaction for finally removing the protecting group of the 5'-hydroxyl group of the oligonucleic acid, and can be performed by reacting an acid on the oligo-RNA having cleaved from the solid support.

Examples of the "acid" to be used in the step may include, trichloroacetic acid, dichloroacetic acid and acetic acid. The acid diluted in a suitable solvent can be used in the step. The solvent is not specifically limited unless it is involved in the reaction, and may include, for example, methylene chloride, acetonitrile, water, a buffer wherein pH is in the range from 2 to 5 and mixtures thereof Examples of the "buffer solution" may include an acetate buffer. The reaction temperature in the reaction is preferably in the range of 20° C. to 50° C. The reaction time for deprotection varies depending on the kind of the oligonucleic acid derivative (11), the acid and the reaction temperature, and may be in the range of 1 minute to 1 hour. The amount of the reagent to be used may be in the range of 0.8 to 100 mol per mol of the oligonucleic acid derivative attached to the solid phase support, and preferably 1 to 10 mol per mol of the compound attached to the solid support.

(8) Step H:

Process for isolating and purifying the oligo-RNA (A) produced by step G.

The step of isolating and purifying is a step for isolating and purifying a desired oligo-RNA from the above reaction mixture with a known method for isolating and purifying which may include, for example, extraction, concentration, neutralization, filtration, centrifugal separation, recrystallization, reverse-phase column chromatography ($C_8$ to $C_{18}$), reverse phase cartridge column ($C_8$ to $C_{18}$), cation-exchange column chromatography, anion-exchange column chromatography, gel filtration column chromatography, high performance liquid chromatography, dialysis, ultrafiltration and combinations thereof.

Examples of the "eluent" may include acetonitrile, methanol, ethanol, isopropyl alcohol, water and solvent mixed at an arbitrary ratio. In this case, for example, pH of the solution can be controlled to be in the range of pH 1 to 9 by adding sodium phosphate, potassium phosphate, sodium chloride, potassium chloride, ammonium acetate, triethylammonium acetate, sodium acetate, potassium acetate, tris-hydrochloric acid or ethylenediaminetetraacetic acid as an additive in a concentration of 1 mM to 2 M.

The oligo-RNA (A) of desired chain length can be produced by repeating operation of step A-step D.

In addition, in the method, the compound (27a) wherein $R^{4a}$ is the substituent (4), the compound (27a) wherein $R^{4a}$ is H or acyl, or the compound (27b) wherein $R^2$ is alkyloxy are used. When using the compound (27a) wherein $R^{4a}$ is H or acyloxy or the compound (27b) wherein $R^2$ is alkyloxy as a starting material, it is necessary to use one or more units of the phosphoramidite compounds according to the present invention as a nucleic acid monomer compound.

EXAMPLES

The present invention will now be described in more detail with reference to Examples, to which, however, the present invention is not limited.

Reference Example 1

Chloromethyl 2-cyanoethyl ether

Step 1

Production of methylthiomethyl 2-cyanoethyl ether

3-Hydroxypropionitrile (32 g, 450 mmol) was dissolved in 450 mL of dimethylsulfoxide, and 324 mL of acetic anhydride and 231 mL of acetic acid were added thereto, and the reaction solution was stirred at room temperature for 24 hours. Sodium bicarbonate (990 g) was dissolved in 4.5 L of water, and the reaction solution was added to the aqueous sodium bicarbonate solution dropwise over 1 hour, and was subjected to extraction with ethyl acetate, and the extract was dried over anhydrous magnesium sulfate, and the solvent was distilled off. The obtained oily product was purified by silica gel column chromatography to obtain 41 g of methylthiomethyl 2-cyanoethyl ether as a colorless oily product (yield 70%).

$^1$H-NMR (CDCl$_3$): 2.18 (s, 3H), 2.66 (t, 2H, J=6.3 Hz), 3.77 (t, 2H, J=6.3 Hz), 4.69 (s, 2H)

Step 2

Production of chloromethyl 2-cyanoethyl ether

Methylthiomethyl 2-cyanoethyl ether (3.3 g, 25 mmol) was dissolved in 70 mL of methylene chloride, and 2 mL of sulfuryl chloride (25 mmol) was added dropwise, and the reaction was further performed at room temperature for 1 hour. After the reaction completed, the solvent was distilled off under reduced pressure to obtain 2.5 g of the objective compound as a colorless oily product (yield 85%).

Boiling point: 84° C.-85° C. (0.3 Torr)

$^1$H-NMR (CDCl$_3$): 2.72 (t, 2H, J=6.3 Hz), 3.92 (t, 2H, J=6.3 Hz), 5.52 (s, 2H)

Reference Example 2

5'-O-(4,4'-dimethoxytrityl)-2'-O-(2-cyanoethoxymethyl)uridine 3'-O-(2-cyanoethyl N,N-diisopropylphosphoramidite)

Step 1

Production of 5'-O-(4,4'-dimethoxytrityl)-2'-O-(2-cyanoethoxymethyl)uridine

5'-O-(4,4'-Dimethoxytrityl)uridine (546 mg, 1 mmol) was dissolved in 4 mL of 1,2-dichloroethane, and 452 mg of diisopropylethylamine (3.5 mmol) was added thereto, and 365 mg of dibutylstannyl dichloride (1.2 mmol) was further added thereto. The reaction was performed at room temperature for 1 hour. Subsequently, the reaction was performed at 80° C., and 155.4 mg of chloromethyl 2-cyanoethyl ether (1.3 mmol) was added dropwise, and the reaction solution was stirred for 30 minutes. After the reaction completed, the reaction solution was added into an aqueous saturated sodium bicarbonate solution, and was subjected to extraction with methylene chloride, and the extract was dried over anhydrous magnesium sulfate, and the solvent was distilled off. The obtained mixture was purified by 30 g of silica gel column chromatography to obtain 5'-O-(4,4'-dimethoxytrityl)-2'-O-(2-cyanoethoxymethyl)uridine (197 mg, yield 34%).

$^1$H-NMR (CDCl$_3$): 2.47 (d, 1H, J=7.8 Hz), 2.69 (t, 2H, J=6.3 Hz), 3.55 (dd, 1H, J=11.3, 2.2 Hz), 3.62 (dd, 1H, J=11.3, 2.2 Hz), 3.83 (s, 6H), 3.87 (t, 2H, J=6.3 Hz), 4.07-4.08 (m, 1H), 4.32 (dd, 1H, J=5.3, 1.9 Hz), 4.54 (q, 1H, J=5.3 Hz), 4.94, 5.11 (2d, 2H, J=6.9 Hz), 5.32 (d, 1H, J=8.2 Hz), 6.00 (d, 1H, J=1.9 Hz), 6.85-6.88 (m, 4H), 7.29-7.41 (m, 9H), 8.02 (d, 1H, J=8.2 Hz), 8.53 (brs, 1H)

ESI-Mass: 652[M+Na]$^+$

Step 2

Production of 5'-O-(4,4'-dimethoxytrityl)-2'-O-(2-cyanoethoxymethyl)uridine 3'-O-(2-cyanoethyl N,N-diisopropylphosphoramidite)

5'-O-(4,4'-Dimethoxytrityl)-2'-O-(2-cyanoethoxymethyl) uridine (209 g, 0.332 mmol) was dissolved in 2 mL of acetonitrile obtained in Step 1 and 23 mg of tetrazole (0.332 mmol), and 150 mg of 2-cyanoethyl N,N,N',N'-tetraisopropylphosphorodiamidite (0.498 mmol) were added dropwise, and the reaction was performed at 45° C. for 1.5 hours. After the reaction completed, the reaction solution was mixed with an aqueous saturated sodium bicarbonate solution, and was subjected to extraction with ethyl acetate, and the extract was dried over anhydrous magnesium sulfate, and the solvent was distilled off. The obtained mixture was purified by 20 g of silica gel column chromatography to obtain the objective compound (200 mg, yield 73%).

ESI-Mass: 852[M+Na]$^+$

Reference Example 3

2'-O-(2-cyanoethoxymethyl)uridine

Step 1

Production of 3',5'-O-(tetraisopropyldisiloxane-1,3-diyl)-2'-O-(2-cyanoethoxymethyl)uridine 3',5'-O-(tetraisopropyldisiloxane-1,3-diyl)uridine 150 mg (0.3 mmol) was dissolved in 7 mL of THF under an argon atmosphere, and 54 mg of methylthiomethyl 2-cyanoethyl ether (0.4 mmol) and 100 mg of molecular sieve 4 A were added, and the reaction solution was stirred for 10 minutes. The reaction was performed at 0° C., and 2 mL of a solution of trifluoromethanesulfonic acid (10 mg, 0.06 mmol) in THF was added. Then, and 92 mg of N-iodosuccinimide (0.4 mmol) was added, and the reaction solution was stirred for 1 hour. After the reaction completed, the reaction solution was filtrated with a celite and washed with methylene chloride, and the obtained organic layer was washed with 1 M aqueous sodium hydrogen thiosulfate solution. The organic layer was washed with aqueous saturated sodium bicarbonate solution, and dried over anhydrous magnesium sulfate, and the solvent was distilled off. The obtained residue was purified by thin-layer chromatography to obtain 3',5'-O-(tetraisopropyldisiloxan-1,3-diyl)-2'-O-(2-cyanoethoxymethyl)uridine (150 mg, yield 85%).

$^1$H-NMR (CDCl$_3$): 0.97-1.12 (m, 28H), 2.68-2.73 (m, 2H), 3.78-3.86 (m, 1H), 3.96-4.05 (m, 2H), 4.12-4.30 (m, 4H), 5.0-5.04 (m, 2H), 5.70 (d, 1H, J=8.2 Hz), 5.75 (s, 1H), 7.90 (d, 1H, J=8.2 Hz), 9.62 (brs, 1H)

ESI-Mass: 570[M+H]$^+$

Step 2

Production of 2'-O-(2-cyanoethoxymethyl)uridine

3',5'-O-(Tetraisopropyldisiloxan-1,3-diyl)-2'-O-(2-cyanoethoxymethyl)uridine (200 mg, 0.35 mmol) obtained in step 1 was dissolved in 2 mL of methanol, and 65 mg of ammonium fluoride (1.76 mmol) was added thereto, and the reaction solution was stirred with heating at 50° C. for 5 hours. After air-cooling, acetonitrile was added to the reaction solution. The solution was stirred, and was filtrated and concentrated. The obtained residue was purified by silica gel column chromatography to obtain the objective compound (108 mg, yield 94%).

$^1$H-NMR (CD$_3$OD): 2.72-2.76 (t, 2H, J=6.2 Hz), 3.68-3.92 (m, 4H) 4.00-4.03 (m, 1H), 4.26-4.32 (m, 2H), 4.81-4.95 (m, 2H), 5.71 (d, 1H, J=8.1 Hz), 6.00 (d, 1H, J=3.3 Hz), 8.10 (d, 1H, J=8.1 Hz)

ESI-Mass: 350[M+Na]$^+$

Reference Example 4

Production of 5'-O-(4,4'-dimethoxytrityl)-2'-O-(2-cyanoethoxymethyl)uridine

2'-O-(2-Cyanoethoxymethyl)uridine (14 g, 43 mmol) was subjected to azeotropic distillation with pyridine, and then was dried with a vacuum pump for 30 minutes. The residue was dissolved in 300 mL of THF, and 68 g of pyridine (856 mmol), and 20 g of molecular sieve 4 A was added under an argon atmosphere, and the mixture was stirred for 10 minutes. To the solution was added 19.6 g of 4,4'-dimethoxytritylchloride (57.8 mmol) by 3 portions every 1 hour, and the mixture was further stirred for 1 hour. After 10 mL of methanol was added and the reaction solution was stirred for 2 minutes, the reaction solution was filtrated with a celite, and was washed with ethyl acetate. After concentrating the filtrate, the residue was dissolved in ethyl acetate, and was washed with a saturated aqueous sodium bicarbonate solution. After the organic layer was washed with saturated brine and dried over anhydrous magnesium sulfate, the solvent was distilled off. The obtained residue was purified by silica gel chromatography to obtain the objective compound (26.5 g, yield 98%).

Reference Example 5

$N^4$-acetyl-5'-O-(4,4'-dimethoxytrityl)-2'-O-(2-cyanoethoxymethyl) cytidine 3'-O-(2-cyanoethyl N,N-diisopropylphosphoramidite)

Step 1

Production of $N^4$-acetyl-5'-O-(4,4'-dimethoxytrityl)-2'-O-(2-cyanoethoxymethyl) cytidine $N^4$-Acetyl-5'-O-(4,4'-dimethoxytrityl)cytidine (588 mg, 1 mmol) was dissolved in 4 mL of 1,2-dichloroethane, and 452 mg of diisopropylethylamine (3.5 mmol) was added thereto, and then 365 mg of dibutylstannyl dichloride (1.2 mmol) was further added. The reaction was performed at room temperature for 1 hour. Then, the reaction was performed at 80° C., and 155.4 mg of chloromethyl 2-cyanoethyl ether (1.3 mmol) was added dropwise, and the solution was stirred for 60 minutes. After the reaction completed, the reaction solution was added into an aqueous saturated sodium bicarbonate solution, and was extracted with methylene chloride. The extract was dried over anhydrous magnesium sulfate, and the solvent was distilled off. The obtained mixture was purified by 30 g of silica gel column chromatography to obtain $N^4$-acetyl-5'-O-(4,4'-dimethoxytrityl)-2'-O-(2-cyanoethoxymethyl) cytidine (219 mg, yield 35%).

$^1$H-NMR (CDCl$_3$): 2.19 (s, 3H), 2.56 (d, 1H, J=8.8 Hz), 2.65 (t, 2H, J=6.2 Hz), 3.55 (dd, 1H, J=10.5, 2.5 Hz), 3.63 (dd, 1H, J=10.5, 2.5 Hz), 3.82 (s, 6H), 3.86 (t, 2H, J=6.2 Hz), 4.09-4.14 (m, 1H) 4.28 (d, 1H, J=5.1 Hz), 4.44-4.49 (m, 1H), 4.97, 5.24 (2d, 2H, J=6.9 Hz), 5.96 (s, 1H), 6.86-6.88 (m, 4H), 7.09 (d, 1H, J=6.9 Hz), 7.26-7.42 (m, 9H), 8.48 (d, 1H, J=6.9 Hz), 8.59 (brs, 1H)

ESI-Mass: 693[M+Na]$^+$

Step 2

Production of $N^4$-acetyl-5'-O-(4,4'-dimethoxytrityl)-2'-O-(2-cyanoethoxymethyl) cytidine 3'-O-(2-cyanoethyl N,N-diisopropylphosphoramidite)

$N^4$-Acetyl-5'-O-(4,4'-dimethoxytrityl)-2'-O-(2-cyanoethoxymethyl) cytidine (205 mg, 0.306 mmol) obtained in Step 1 was dissolved in 2 mL of methylene chloride, and 105 mg of diisopropylethylamine (0.812 mmol) was added, and 116 mg of 2-cyanoethyl N,N-diisopropyl chlorophosphoramidite (0.49 mmol) was added dropwise. The reaction solution was reacted at room temperature for 1 hour. After the reaction completed, the solvent was distilled off and the obtained mixture was purified by 20 g of silica gel column chromatography to obtain the objective compound (242 mg, yield 91).

ESI-Mass: 871[M+H]$^+$

Reference Example 6

$N^4$-acetyl-2'-O-(2-cyanoethoxymethyl)cytidine

Step 1

Production of $N^4$-acetyl-3',5'-O-(tetraisopropyldisiloxane-1,3-diyl)-2'-O-(2-cyanoethoxymethyl)cytidine $N^4$-acetyl-3',5'-O-(1,3-tetraisopropyldisiloxane-diyl)cytidine 1.00 g (1.89 mmol) and methylthiomethyl 2-cyanoethyl ether 500 mg (3.79 mmol) were mixed, and the mixture was dissolved in mixed solvent of 10 mL of toluene and 10 mL of THF. Subsequently, 975 mg of silver trifluoromethanesulfonate was added and was dried by adding molecular sieves 4 A. Under ice cooling, 370 mg of N-bromosuccinimide (2.08 mmol) was added, and the solution was stirred for 10 minutes in the reaction vessel shielded from light. Furthermore, 70 mg of N-bromosuccinimide (0.39 mmol) was added and stirred for 25 minutes. After the reaction completed, the reaction solution was diluted with methylene chloride, and was washed with an aqueous saturated sodium bicarbonate solution. The extract was dried over anhydrous sodium sulfate, and the solvent was distilled off. The obtained mixture was purified by silica gel column chromatography to obtain $N^4$-acetyl-3',5'-O-(tetraisopropyldisiloxan-1,3-diyl)-2'-O-(2-cyanoethoxymethyl)cytidine (936 mg, yield 81%).

$^1$H-NMR (CDCl$_3$): 0.90-1.11 (m, 28H), 2.28 (s, 3H), 2.62-2.79 (m, 2H) 3.78-3.89 (m, 1H), 3.96-4.04 (m, 2H), 4.19-4.23 (m, 3H), 4.30 (d, 1H, J=13.6 Hz), 5.00 (d, 1H, J=6.8 Hz), 5.09 (d, 1H, J=6.8 Hz), 5.77 (s, 1H), 7.44 (d, 1H, J=7.5 Hz), 8.30 (d, 1H, J=7.5 Hz), 10.13 (s, 1H)

ESI-Mass: 611[M+H]$^+$

Step 2

Production of $N^4$-acetyl-2'-O-(2-cyanoethoxymethyl) cytidine $N^4$-acetyl-3',5'-O-(tetraisopropyldisiloxane-1,3-diyl)-2'-O-(2-cyanoethoxymethyl)cytidine (500 mg, 0.819 mmol) obtained in step 1 was dissolved in a mixed solvent of 2.5 mL of THF and 2.5 mL of methanol, and 150 mg of ammonium fluoride (4.10 mmol) was added, and then the reaction solution was reacted at 50° C. for 4 hours. After the reaction completed, the reaction solution was diluted with acetonitrile and filtrated, and the solvent was distilled off. The obtained mixture was purified by silica gel column chromatography to obtain the objective compound (210 mg, yield 70%).

$^1$H-NMR (D$_2$O): 2.13 (s, 3H), 2.66-2.71 (m, 2H), 3.72-3.78 (m, 3H), 3.90 (dd, 1H, J=13.0, 2.6 Hz), 4.06-4.11 (m, 1H), 4.20 (dd, 1H, J=7.1, 5.2 Hz), 4.29 (dd, 1H, J=5.1, 2.9 Hz), 4.83 (d, 1H, J=7.2 Hz), 4.94 (d, 1H, J=7.2 Hz), 5.95 (d, 1H, J=2.9 Hz), 7.25 (d, 1H, J=7.6 Hz), 8.25 (d, 1H, J=7.6 Hz)

ESI-Mass: 391[M+Na]$^+$

Reference Example 7

Production of $N^4$-acetyl-5'-O-(4,4'-dimethoxytrityl)-2'-O-(2-cyanoethoxymethyl) cytidine 2'-O-(2-Cyanoethoxymethyl)cytidine (9.9 g, 26.8 mmol) was subjected to azeotropic distillation with pyridine, and then was dried with a vacuum pump for 30 minutes. The residue was dissolved in 190 mL of THF, and 43 g of pyridine (538 mmol) and 20 g of molecular sieve 4 A were added under an argon atmosphere, and the mixture was stirred for 10

Reference Example 8

N$^2$-acetyl-5'-O-(4,4'-dimethoxytrityl)-2'-O-(2-cyanoethoxymethyl) guanosine 3'-O-(2-cyanoethyl N,N-diisopropylphosphoramidite)

Step 1

Production of N$^2$-acetyl-5'-O-(4,4'-dimethoxytrityl)-2'-O-(2-cyanoethoxymethyl) guanosine N$^2$-Acetyl-5'-O-(4,4'-dimethoxytrityl)guanosine (627 mg, 1 mmol) was dissolved in 4 mL of 1,2-dichloroethane, and 452 mg of diisopropylethylamine (3.5 mmol) was added, and then 365 mg of dibutylstannyl dichloride (1.2 mmol) was added. And then, the reaction solution was reacted at room temperature for 1 hour. Then, the reaction was performed at 80° C., and 155.4 mg of chloromethyl 2-cyanoethyl ether (1.3 mmol) was added dropwise, and the solution was stirred for 60 minutes. After the reaction completed, the reaction solution was mixed with an aqueous saturated sodium bicarbonate solution, and was subjected to extraction with methylene chloride. The extract was dried over anhydrous magnesium sulfate, and the solvent was distilled off. The obtained mixture was purified by 30 g of silica gel column chromatography to obtain N$^2$-acetyl-5'-O-(4,4'-dimethoxytrityl)-2'-O-(2-cyanoethoxymethyl) guanosine (450 mg, yield 63%).

$^1$H-NMR (CDCl$_3$): 1.92 (s, 3H), 2.47-2.51 (m, 2H), 2.68 (brs, 1H), 3.30 (dd, 1H, J=10.7, 3.8 Hz), 3.47 (dd, 1H, J=10.7, 3.8 Hz), 3.55-3.60 (m, 1H), 3.65-3.70 (m, 1H), 3.74, 3.75 (2s, 6H), 4.22-4.23 (m, 1H), 4.55-4.58 (m, 1H), 4.78, 4.83 (2d, 2H, J=7.0 Hz), 5.01 (t, 1H, J=5.1 Hz), 5.99 (d, 1H, J=5.1 Hz), 6.76-6.79 (m, 4H), 7.17-7.44 (m, 9H), 7.88 (s, 1H), 8.36 (brs, 1H), 12.06 (brs, 1H)

Step 2

Production of N$^2$-acetyl-5'-O-(4,4'-dimethoxytrityl)-2'-O-(2-cyanoethoxymethyl) guanosine 3'-O-(2-cyanoethyl N,N-diisopropylphosphoramidite)

N$^2$-acetyl-5'-O-(4,4'-dimethoxytrityl)-2'-O-(2-cyanoethoxymethyl) guanosine (400 mg, 0.563 mmol) obtained in step 1 was dissolved in 2 mL of methylene chloride, and 181 mg of diisopropylethylamine (1.4 mmol) was added, and 161 mg of 2-cyanoethyl N,N-diisopropylchloro phosphoramidite (0.68 mmol) was added dropwise. Then, the reaction was performed at room temperature for 1 hour. After the reaction completed, the solvent was distilled off and the obtained mixture was purified by 20 g of silica gel column chromatography to obtain the objective compound (471 mg, yield 92%)

minutes. To the reaction solution was added 11.8 g of 4,4'-dimethoxytrityl chloride 11.8 g (34.9 mmol) by 3 portions every 1 hour, and the mixture was further stirred for 1 hour. After 2 mL of methanol was added and the reaction solution was stirred for 2 minutes, the reaction solution was filtrated with a celite, and was washed with ethylacetate. After concentrating the filtrate with evaporation, the residue was dissolved in ethyl acetate, and was separated with a saturated aqueous sodium bicarbonate solution. After the organic layer was washed with saturated brine and dried over anhydrous magnesium sulfate, the solvent was distilled off. The obtained residue was purified by silica gel chromatography to obtain the objective compound (15 g, yield 83%).

Reference Example 9

N$^6$-acetyl-5'-O-(4,4'-dimethoxytrityl)-2'-O-(2-cyanoethoxymethyl) adenosine 3'-O-(2-cyanoethyl N,N-diisopropylphosphoramidite)

Step 1

Production of N$^6$-acetyl-5'-O-(4,4'-dimethoxytrityl)-2'-O-(2-cyanoethoxymethyl) adenosine N$^6$-Acetyl-5'-O-(4,4'-dimethoxytrityl)adenosine (22.0 g, 36.0 mmol) was dissolved in 170 mL of 1,2-dichloroethane, and 16.3 g of diisopropylethylamine (126 mmol) was added, and 12.1 g of dibutylstannyl dichloride (39.7 mmol) was added subsequently. Then, the reaction was performed at room temperature for 1 hour. Then, the reaction solution was heated up to 80° C., and 4.30 g of chloromethyl 2-cyanoethyl ether (36.0 mmol) was added dropwise, and the solution was stirred for 30 minutes. After the reaction completed, the reaction solution was added to an aqueous saturated sodium bicarbonate solution, and was subjected to extraction with methylene chloride. The extract was dried over anhydrous magnesium sulfate, and the solvent was distilled off. The obtained mixture was purified by silica gel column chromatography to obtain N$^6$-acetyl-5'-O-(4,4'-dimethoxytrityl)-2'-O-(2-cyanoethoxymethyl) adenosine (7.47 g, yield 33%).

$^1$H-NMR (CDCl$_3$): 2.51 (t, 2H, J=6.2 Hz), 2.58 (d, 1H, J=5.5 Hz), 2.61 (s, 3H), 3.45 (dd, 1H, J=10.7, 4.0 Hz), 3.54 (dd, 1H, J=10.7, 3.2 Hz), 3.62-3.79 (m, 2H), 3.79 (s, 6H), 4.25 (br.q, 1H, J=4.6 Hz), 4.59 (q, 1H, J=5.2 Hz), 4.87-4.94 (m, 3H), 6.23 (d, 1H, J=4.4 Hz), 6.80-6.83 (m, 4H), 7.22-7.32 (m, 7H), 7.40-7.43 (m, 2H), 8.20 (s, 1H), 8.61 (brs, 1H), 8.62 (s, 1H)

ESI-Mass: 695[M+H]$^+$

Step 2

Production of N$^6$-acetyl-5'-O-(4,4'-dimethoxytrityl)-2'-O-(2-cyanoethoxymethyl) adenosine 3'-O-(2-cyanoethyl N,N-diisopropylphosphoramidite)

N$^6$-Acetyl-5'-O-(4,4'-dimethoxytrityl)-2'-O-(2-cyanoethoxymethyl)adenosine (10.0 g, 14.4 mmol) obtained in step 1 was dissolved in 75 mL of methylene chloride, and 4.7 g of diisopropylethylamine (36 mmol) was added, and 4.82 g of 2-cyanoethyl N,N-diisopropylchloro phosphoramidite (20.3 mmol) was added dropwise. Then, the reaction was performed at room temperature for 1 hour. After the reaction completed, the solvent was distilled off and the obtained mixture, in which about 30 mL of the solvent remained, was purified by silica gel column chromatography to obtain the objective compound (12.0 g, yield 93%).

ESI-Mass: 895[M+H]$^+$

Reference Example 10

N$^6$-acetyl-2'-O-(2-cyanoethoxymethyl)adenosine

Step 1

Production of N$^6$-acetyl-3',5'-O-(tetraisopropyldisiloxan-1,3-diyl)-2'-O-(2-cyanoethoxymethyl)adenosine To 8 mL of methylene chloride were suspended 245 mg of N-iodosuccinimide (1.09 mmol) and 280 mg of silver trifluoromethanesulfonate (1.09 mmol), and the solution was dried by adding molecular sieve 4 A. To the reaction solution was added a solution of $N^6$-acetyl-3',5'-O-(tetraisopropyldisiloxane-1,3-diyl)adenosine (400 mg, 0.73 mmol) and 145 mg of methylthiomethyl 2-cyanoethyl ether (1.11 mmol) in 4 mL of methylene chloride under ice cooling, and the reaction mixture was stirred for 3 hours. After the reaction completed, the reaction mixture was diluted with methylene chloride, and was washed with aqueous sodium thiosulfate solution and aqueous saturated sodium bicarbonate solution. The extract was dried over anhydrous magnesium sulfate, and the solvent was distilled off. The obtained mixture was purified by silica gel column chromatography to obtain $N^6$-acetyl-3',5'-O-(tetraisopropyldisiloxan-1,3-diyl)-2'-O-(2-cyanoethoxymethyl)adenosine (201 mg, yield 45%).

$^1$H-NMR (CDCl$_3$): 0.98-1.11 (m, 28H), 2.62 (s, 3H), 2.69 (td, 2H, J=6.5, 1.5 Hz), 3.81-3.89 (m, 1H), 4.02-4.09 (m, 2H), 4.17 (d, 1H, J=9.4 Hz), 4.28 (d, 1H, J=13.4 Hz), 4.50 (d, 1H, J=4.5 Hz), 4.67 (dd, 1H, J=8.8, 4.5 Hz), 5.02 (d, 1H, J=7.0 Hz), 5.08 (d, 1H, J=7.0 Hz), 6.10 (s, 1H), 8.34 (s, 1H), 8.66 (s, 1H), 8.67 (s, 1H)

ESI-Mass: 636[M+H]$^+$

Step 2

Production of $N^6$-acetyl-2'-O-(2-cyanoethoxymethyl)adenosine $N^6$-acetyl-3',5'-O-(tetraisopropyldisiloxane-1,3-diyl)-2'-O-(2-cyanoethoxymethyl)adenosine (300 mg, 0.47 mmol) obtained in step 1 was dissolved in a mixed solvent of 0.1 mL of acetic acid and 2 mL of 0.5 M TBAF/THF solution, and the reaction solution was stirred at room temperature for 2 hours. After the reaction completed, the obtained reaction mixture was purified by silica gel column chromatography to obtain the objective compound (160 mg, yield 86%).

$^1$H-NMR (DMSO-d$_6$): 2.25 (s, 3H), 2.53-2.68 (m, 2H), 3.41-3.46 (m, 1H), 3.56-3.64 (m, 2H), 3.69-3.73 (m, 1H), 4.00-4.01 (m, 1H), 4.36-4.37 (m, 1H), 4.72-4.78 (m, 3H), 5.20 (bt, 2H), 5.41 (d, 1H, J=5.2 Hz), 6.17 (d, 1H, J=5.7 Hz), 8.66 (s, 1H), 8.72 (s, 1H), 10.72 (s, 1H)

ESI-Mass: 415[M+Na]$^+$

Reference Example 11

Production of $N^6$-acetyl-2'-O-(2-cyanoethoxymethyl)adenosine $N^6$-Acetyl-2'-O-(2-cyanoethoxymethyl)adenosine (9.50 g, 24.2 mmol) was dissolved in 100 mL of dehydrated pyridine, and then was dried by concentration. Then, the residue was dissolved in 100 mL of dehydrated pyridine under an argon atmosphere. Under ice cooling, 10.7 g of 4,4'-dimethoxytrityl chloride (31.2 mmol) was added, and the reaction was performed at room temperature for 1 hour and 20 minutes. After the reaction completed, the reaction solution was diluted with methylene chloride, and was washed with water. The extract was dried over anhydrous sodium sulfate, and the solvent was distilled off. The obtained mixture was purified by silica gel column chromatography to obtain the objective compound (13.8 g, yield 82%).

Reference Example 12

$N^2$-phenoxyacetyl-5'-O-(4,4'-dimethoxytrityl)-2'-O-(2-cyanoethoxy methyl)guanosine 3'-O-(2-cyanoethyl N,N-diisopropylphosphoramidite)

Step 1

Production of $N^2$-phenoxyacetyl-5'-O-(4,4'-dimethoxytrityl)-2'-O-(2-cyanoethoxy methyl)guanosine $N^2$-Phenoxyacetyl-5'-O-(4,4'-dimethoxytrityl)guanosine (720 mg, 1 mmol) was dissolved in 4 mL of 1,2-dichloroethane, and 452 mg of diisopropylethylamine (3.5 mmol) was added, and 365 mg of dibutylstannyl dichloride (1.2 mmol) was added subsequently. Then, the reaction was performed at room temperature for 1 hour. Then, the reaction was performed at 80° C., and 155.4 mg of chloromethyl 2-cyanoethyl ether (1.3 mmol) was added dropwise, and the solution was stirred for 60 minutes. After the reaction completed, the reaction solution was mixed with an aqueous saturated sodium bicarbonate solution, and was subjected to extraction with methylene chloride. The extract was dried over anhydrous magnesium sulfate, and the solvent was distilled off. The obtained mixture was purified by 30 g of silica gel column chromatography to obtain $N^2$-phenoxyacetyl-5'-O-(4,4'-dimethoxytrityl)-2'-O-(2-cyanoethoxy methyl)guanosine (384 mg, yield 48%).

$^1$H-NMR (CDCl$_3$): 2.47-2.51 (m, 2H), 2.58 (brs, 1H), 3.42 (dd, 1H, 10.1, 3.8 Hz), 3.46 (dd, 1H, J=10.1, 3.8 Hz), 3.53-3.57 (m, 1H), 3.69-3.73 (m, 1H), 3.77 (s, 6H), 4.24-4.26 (m, 1H), 4.48-4.50 (m, 1H), 4.61-4.65 (m, 2H), 4.83, 4.87 (2d, 2H, J=7.0 Hz), 4.88 (t, 1H, J=5.7 Hz), 6.05 (d, 1H, J=5.7 Hz), 6.80-6.82 (m, 4H), 6.92-6.96 (m, 3H), 7.07-7.11 (m, 2H), 7.20-7.42 (m, 9H), 7.84 (s, 1H), 8.99 (s, 1H), 11.81 (brs, 1H)

ESI-Mass: 825[M+Na]$^+$

Step 2

Production of $N^2$-phenoxyacetyl-5'-O-(4,4'-dimethoxytrityl)-2'-O-(2-cyanoethoxy methyl)guanosine 3'-O-(2-cyanoethyl N,N-diisopropylphosphoramidite)

$N^2$-Phenoxyacetyl-5'-O-(4,4'-dimethoxytrityl)-2'-O-(2-cyano ethoxymethyl)guanosine (320 mg, 0.399 mmol) obtained in step 1 was dissolved in 4 mL of methylene chloride, and 128.8 mg of diisopropylethylamine (0.996 mmol) was added, and 141.5 mg of 2-cyanoethyl N,N-diisopropylchlorophosphoramidite (0.598 mmol) was added dropwise. Then, the reaction was performed at room temperature for 1 hour. After the reaction completed, the solvent was distilled off and the obtained mixture was purified by 30 g of silica gel column chromatography to obtain the objective compound (316 mg, yield 79%)

ESI-Mass: 1,003[M+H]$^+$

Reference Example 13

$N^2$-phenoxyacetyl-2'-O-(2-cyanoethoxymethyl)guanosine

Step 1

Production of $N^2$-phenoxyacetyl-3',5'-O-(tetraisopropyldisiloxane-1,3-diyl)-2'-O-(2-cyanoethoxymethyl)guanosine $N^2$-phenoxyacetyl-3',5'-O-(1,3-tetraisopropyldisiloxane-1,3-diyl) guanosine (2.0 g, 3.0 mmol) was dissolved in 16 mL of THF, and 0.99 g of methylthiomethyl 2-cyanoethyl ether (7.6 mmol) and 1.0 g of molecular sieve 4 A were added, and the reaction solution was stirred at −45° C. for 10 minutes under an argon atmosphere. After a solution of 0.68 g of trifluoromethanesulfonic acid (4.5 mmol) in 5 mL of THF was added and the reaction solution was stirred, 1.02 g of N-iodosuccinimide (4.5 mmol) are added, and the reaction solution was stirred for 15 minutes. After saturated aqueous sodium bicarbonate solution was added to the reaction solution and then the reaction solution was filtrated, the organic layer was washed with 1 M aqueous sodium hydrogen thiosulfate solution. Further, the reaction solution was washed with water and saturated brine sequentially, and the extract was dried over anhydrous magnesium sulfate, and the solvent was distilled off. The obtained residue was purified by silica gel chromatography to obtain $N^2$-phenoxyacetyl-3',5'-O-(tetraisopropyldisiloxan-1,3-diyl)-2'-O-(2-cyanoethoxymethyl)guanosine (2.0 g, yield 89%).

$^1$H-NMR (CDCl$_3$): 0.99-1.11 (m, 28H), 2.59-2.77 (m, 2H), 3.82-4.05 (m, 3H), 4.15 (d, 1H, J=9.3 Hz), 4.25-4.35 (m, 2H), 4.52-4.56 (dd, 1H, J=9.3, 4.3 Hz), 5.00, 5.07 (2d, 2H, J=7.2 Hz), 5.95 (s, 1H) 6.99-7.12 (m, 3H), 7.35-7.40 (m, 2H), 8.09 (s, 1H), 9.38 (brs, 1H), 11.85 (brs, 1H)

ESI-Mass: 766[M+Na]$^+$

Step 2

Production of $N^2$-phenoxyacetyl-2'-O-(2-cyanoethoxymethyl)guanosine

The solution consisting of 0.14 mL of acetic acid (0.14 mmol) and 2.83 mL of 1M TBAF in THF (2.83 mmol) was prepared. $N^2$-phenoxyacetyl-3'5'-O-(tetraisopropyldisiloxane-1,3-diyl)-2'-O-(2-cyanoethoxymethyl)guanosine 11.0 g (1.35 mmol) obtained in step 1 was dissolved in 2.83 mL of THF, and the solution prepared above was added, and the reaction was performed at room temperature for 1 hour under an argon atmosphere. The reaction solution was concentrated under reduced pressure, and the residue was dissolved in methylene chloride, and was purified by silica gel column chromatography to obtain the objective compound (0.67 g, yield 99%).

$^1$H-NMR (DMSO-d$_6$): 2.59-2.66 (m, 2H), 3.41-3.63 (m, 4H), 3.98 (m, 1H) 4.32 (m, 1H), 4.58-4.62 (t, 1H, J=5.3 Hz), 4.71-4.78 (dd, 2H, J=13.1, 6.8 Hz), 4.87 (s, 2H), 5.12 (s, 1H) 5.37 (s, 1H), 5.97 (d, 1H, J=6.1 Hz) 6.96-6.99 (m, 3H), 7.28-7.34 (m, 2H), 8.30 (s, 1H) 11.78 (brs, 2H)

ESI-Mass: 500[M−H]$^-$

Reference Example 14

Production of $N^2$-phenoxyacetyl-5'-O-(4,4'-dimethoxytrityl)-2'-O-(2-cyanoethoxymethyl)guanosine $N^2$-Phenoxyacetyl-2'-O-(2-cyanoethoxymethyl)guanosine (660 mg, 1.32 mmol) was subjected to azeotropic distillation with pyridine, and then was dried with a vacuum pump for 30 minutes. The residue was dissolved in 9 mL of THF, and 2.1 g of pyridine (26.4 mmol) and 600 mg of molecular sieve 4 A were added under an argon atmosphere, and the reaction solution was stirred for 10 minutes. To the solution was added 540 mg of 4,4'-dimethoxytritylchloride (1.58 mmol) by 3 portions every 1 hour, and the reaction solution was further stirred for 1 hour. After 2 mL of methanol was added and the reaction solution was stirred for 2 minutes, the reaction solution was filtrated with a celite, and was washed with ethyl acetate. After concentrating the filtrate with evaporation, the residue was dissolved in ethyl acetate, and was separated with a saturated aqueous sodium bicarbonate solution. After the organic layer was washed with saturated brine and dried over anhydrous magnesium sulfate, the solvent was distilled off. The obtained residue was purified by silica gel chromatography to obtain the objective compound (800 mg, yield 75%).

Reference Example 15

$N^6$-acetyl-3',5'-O-(tetraisopropyldisiloxane-1,3-diyl)-2'-O-(2-cyanoethoxymethyl)adenosine Step 1

Production of $N^6$-acetyl-3',5'-O-(tetraisopropyldisiloxane-1,3-diyl)-2'-O-methylthiomethyl adenosine $N^6$-Acetyl-3',5'-O-(tetraisopropyldisiloxan-1,3-diyl)adenosine (2.00 g, 3.62 mmol) was dissolved in 25 mL of dimethylsulfoxide, and 17.5 mL of acetic anhydride and 12.5 mL of acetic acid were added, and the reaction solution was stirred at room temperature for 14 hours After the reaction completed, the reaction solution was added to 200 mL of water, extracted with ethyl acetate, and was washed with saturated aqueous sodium bicarbonate solution. The extract was dried over anhydrous sodium sulfate, and the solvent was distilled off. The obtained mixture was purified by silica gel column chromatography to obtain $N^6$-acetyl-3',5'-O-(tetraisopropyldisiloxan-1,3-diyl)-2'-O-methyl thiomethyl adenosine (1.36 g, yield 61%).

$^1$H-NMR (CDCl$_3$): 0.96-1.11 (m, 28H), 2.20 (s, 3H), 2.61 (s, 3H), 4.03 (dd, 1H, J=13.4, 2.4 Hz), 4.18 (d, 1H, J=9.1 Hz), 4.27 (d, 1H, J=13.4 Hz), 4.63-4.71 (m, 2H), 5.00 (d, 1H, J=11.5 Hz), 5.07 (d, 1H, J=11.5 Hz), 6.09 (s, 1H), 8.31 (s, 1H), 8.65 (s, 1H), 8.69 (s, 1H)

ESI-Mass: 635[M+Na]$^+$

Step 2

Production of $N^6$-acetyl-3',5'-O-(tetraisopropyldisiloxane-1,3-diyl)-2'-O-(2-cyanoethoxymethyl)adenosine $N^6$-acetyl-3',5'-O-(tetraisopropyldisiloxane-1,3-diyl)-2'-O-methylthiomethyl adenosine (1.00 g, 1.63 mmol) obtained in step 1 was dissolved in 25 mL of THF. To the reaction solution was added 5.88 g of 3-hydroxypropionitrile (82.7 mmol), and the solution was dried by adding molecular sieves 4 A, and was cooled to −45° C. To the reaction solution were added 440 mg of N-iodosuccinimide (1.96 mmol) and then 490 mg of trifluoromethanesulfonic acid (3.26 mmol), and the reaction solution was stirred at −45° C. for 15 minutes. After the reaction completed, the reaction solution was neutralized by adding triethylamine while cooling, and diluted with methylene chloride. The reaction solution was washed with aqueous sodium thiosulfate solution and saturated aqueous sodium bicarbonate solution, the extract was dried over anhydrous sodium sulfate, and the solvent was distilled off. The obtained mixture was purified by silica gel column chromatography to obtain the objective compound (722 mg, yield 71%).

Reference Example 16

Uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridine The oligo-RNA of the title compound was synthesized by putting commercially available CPG solid support (37 mg, 1 μmol) containing 2'/3'-O-benzoyl-5'-O-(4,4'-dimethoxytrityl)uridine into a column with a glass filter and using an automatic synthesizer for nucleic acid (Expedite™: Applied Biosystems). 5'-O-(4,4'-Dimethoxytrityl)-2'-O-(2-cyanoethoxymethyl)uridine 3'-O-(2-cyanoethyl N,N-diisopropylphosphoramidite) as a nucleic acid monomer compound, tetrazole as a condensation catalyst, iodine solution as an oxidizing agent, acetic anhydride and N-methylimidazole solution as a capping solution were used. After condensing nucleic acid monomer compounds 20 times, the oligo-RNA was cleaved by reacting with 10 M aqueous ethanol solution of methylamine as a cleaving agent at room temperature for 1 to 2 hours, and the protecting groups of each phosphate were removed.

After concentrating the reaction mixture under reduced pressure and removing unnecessary peaks with a reverse phase column (ODS), the reaction solution was purified with an eluent (acetonitrile—50 mM triethylamine—acetate buffer). After concentrating the residue under reduced pressure, the residue was reacted with THF solution of 1M TBAF at room temperature for 1 hour to remove the 2'-hydroxyl protecting group. After desalting the reaction solution, the protecting group of 5' end was removed with 80% acetic acid (treatment at room temperature for 10 minutes). After concentrating under reduced pressure, the aqueous layer was washed with ether, and the high purity objective compound was obtained without purifying.

MALDI-TOF-MS:
Calculated: 6,367.52[M+H]$^+$
Observed: 6,366.50[M+H]$^+$

Reference Example 17

Production of Oligoribonucleic Acid Having Phosphorothioate Bonds

Cytidylyl-[3'→5']-Uridylyl-[3'→5']-Uridylyl-[3'→5']-Adenylyl-[3'→5']-Cytidylyl-[3'→5']-Guanylyl-[3'→5']-Cytidylyl-[3'→5']-Uridylyl-[3'→5']-Guanylyl-[3'→5']-Adenylyl-[3'→5']-Guanylyl-[3'→5']-Uridylyl-[3'→5']-Adenylyl-[3'→5']-Cytidylyl-[3'→5']-Uridylyl-[3'→5']-Uridylyl-[3'→5']-Cytidylyl-[3'→5']-Guanylyl-[3'→5']-Adenylyl-[3'→5']-Thymidylyl-[3'→5']-Thymidine The oligo-RNA of the title compound was synthesized by packing a column with a glass filter and with a commercially available CPG solid support (22 mg, 1 μmol) containing 5'-O-(4,4'-dimethoxytrityl)thymidine and using an automatic synthesizer for nucleic acid (Expedite™: Applied Biosystems). 5'-O-(4,4'-dimethoxytrityl)-2'-O-(2-cyanoethoxymethyl)uridine 3'-O-(2-cyanoethyl N,N-diisopropylphosphoramidite), N$^4$-acetyl-5'-O-(4,4'-dimethoxytrityl)-2'-O-(2-cyanoethoxymethyl) cytidine 3'-O-(2-cyanoethyl N,N-diisopropylphosphoramidite), N$^6$-acetyl-5'-O-(4,4'-dimethoxytrityl)-2'-O-(2-cyanoethoxymethyl) adenosine 3'-O-(2-cyanoethyl N,N-diisopropylphosphoramidite), N$^2$-phenoxyacetyl-5'-O-(4,4'-dimethoxytrityl)-2'-O-(2-cyanoethoxy methyl)guanosine 3'-O-(2-cyanoethyl N,N-diisopropylphosphoramidite) and 5'-O-(4,4'-dimethoxytrityl)cytidine 3'-O-(2-cyanoethyl N,N-diisopropylphosphoramidite) as a nucleic acid monomer compound; benzylmercaptotetrazole as a condensation catalyst; Beaucage reagent (3H-1,2-benzodithiole-3-one-1,1-dioxide) as an oxidizing agent; and acetic anhydride and N-methylimidazole solution as a capping solution were used. After condensing nucleic acid monomer compounds 20 times, cleavage from the CPG solid-phase support, a removal reaction of the protecting group at each phosphate site, and removal of the protecting group for the base were carried out at 40° C. for 4 hours using a mixed liquid of concentrated ammonia water and ethanol (3:1) as a cleaving agent. After concentrating the reaction mixture under reduced pressure, the residue was reacted with 500 μL DMSO solution of 0.5 M TBAF including 2.5 μL of nitromethane to remove the protecting group for the 2'-hydroxyl group of each ribose. Further, 250 μL of 1 M Tris-HCl buffer (pH 7.5) was added thereto, and then, 8 mL of ethanol was added dropwise thereto thereby to precipitate a reaction product. After the reaction product was stored in a refrigerator overnight as such, the supernatant was removed, and the reaction product was purified with ODS column (LiChroprepRP-18). The reaction product was treated with 80% acetic acid to remove 4,4'-dimethoxytrityl, and extracted with ethyl acetate and water. The obtained water phase was distilled off, and the objective compound was obtained (80 OD$_{260}$, yield 40%).

MALDI-TOF-MS:
Calculated: 6,928.4[M+H]$^+$
Observed: 6,930.1[M+H]$^+$

Test Example 1

Deprotection Effect of Amide-Based Solvent

A commercially available CPG solid-phase support (333 mg, 15 μmol) immobilized thereon with 5'-O-(4,4'-dimethoxytrityl)thymidine was placed in a column with a filter, and adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-thymidine was synthesized on the solid phase using an automatic nucleic acid synthesizer (Expedite™: Applied Biosystems), and then, 4,4'-dimethoxytrityl was removed on the solid phase. Cleavage from the CPG solid-phase support, removal of the protecting group at each phosphate site, and removal of the protecting group for the base were carried out at 40° C. for 4 hours using 6 mL of a mixed liquid of concentrated ammonia water and ethanol (3:1) as a cleaving agent to a resin for 2 μmol of oligo-RNA. The resulting reaction mixture was divided into 10 aliquots and concentrated under reduced pressure. Then, a reaction of removing the protecting group for the 2'-hydroxyl group of each ribose was carried out under the deprotection conditions shown in the following Table 1. In each reaction, per 100 μmol of TBAF, 1 μL of nitromethane was added thereto.

After 1 M Tris-HCl buffer (pH 7.5) was added in the same amount as that of the reaction solution, each oligo-RNA was analyzed by HPLC.

Measurement conditions for HPLC are as follows.
Measurement Conditions:
HPLC apparatus:
  Liquid feed unit: LC-10AT (Shimadzu Corporation)
  Detector: SPD-10A (Shimadzu Corporation)
Reverse-phase HPLC column:
  DNAPac PA100<4 mmφ×250 mm>(Dionex Corporation)
  Column temperature: 50° C.

Mobile phase
Gradient: Linear gradient, 20 min (Solution B: 5%-25%)
Solution A: 25 mM Tris-HCl buffer including 10% acetonitrile
Solution B: 25 mM Tris-HCl buffer including 10% acetonitrile and 700 mM sodium perchlorate
Flow rate of mobile phase: 1.5 mL/min
Wavelength for detection with ultraviolet-visible spectrophotometer: 260 nm

| Deprotection effect of amide-based solvent | |
| --- | --- |
| Deprotection conditions | Level of activity of TBAF |
| 1  200 µL of 1 M TBAF/THF solution | Reaction was completed in about 3 hours. |
| 2  Solution obtained by adding 200 µL of DMF to 200 µL of 1 M TBAF/THF solution | Reaction was completed in 1 hour. |
| 3  Solution obtained by adding 100 µL of DMF to 100 µL of 1 M TBAF/THF solution | Reaction was completed in 3 hours. |

As shown in the above Table 1, it is apparent that by adding DMF to a TBAF/THF solution, the reaction time can be shortened and the amount of TBAF reagent can be reduced.

Test Example 2

Deprotection Effect of Amide-Based Solvent and Sulfoxide-Based Solvent

A commercially available CPG solid-phase support (333 mg, 15 µmol) immobilized thereon with 5'-O-(4,4'-dimethoxytrityl)thymidine was placed in a column with a filter, and adenylyl-[3'→5']-cytidylyl-[3'→5']-uridylyl-[3'→5']-guanylyl-[3'→5]-adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-adenylyl-[3'→5']-cytidylyl-[3'→5']-uridylyl-[3'→5']-guanylyl-[3'→5']-thymidine was synthesized on the solid phase using an automatic nucleic acid synthesizer (Expedite™: Applied Biosystems), and then, 4,4'-dimethoxytrityl was removed on the solid phase. Cleavage from the CPG solid-phase support, a removal reaction of the protecting group at each phosphate site, and removal of the protecting group for the base were carried out at 40° C. for 4 hours using 3 mL of a mixed liquid of concentrated ammonia water and ethanol (3:1) as a cleaving agent to a resin for 1 µmol of oligo-RNA. After the resulting reaction mixture was concentrated under reduced pressure, a reaction of removing the protecting group for the 2'-hydroxyl group of each ribose was carried out under the deprotection conditions shown in the following Table 2 at room temperature. In each reaction, per 100 µmol of TBAF, 1 µL of nitromethane was added thereto. Further, per 100 µmol of TBAF, 100 µL of 1 M Tris-HCl buffer (pH 7.5) was added thereto, and then, 2 mL (in the case of Entry 3, 1.5 mL) of ethanol was added dropwise thereto thereby to precipitate a reaction product. After the reaction product was stored in a refrigerator overnight as such, the supernatant was removed, and the reaction product was analyzed by HPLC to confirm the completion of the reaction. The measurement conditions for HPLC were the same as in Test example 1.

TABLE 2

| Deprotection effect of amide-based solvent and sulfoxide-based solvent | |
| --- | --- |
| Deprotection conditions | Level of activity of TBAF |
| 1  500 µL of 1 M TBAF/DMF solution | Reaction was completed in 1 hour. |
| 2  500 µL of 1 M TBAF/DMSO solution | Reaction was completed in 1 hour. |
| 3  400 µL of 0.5 M TBAF/DMSO solution | Reaction was completed in 1 hour. |

As shown in the above Table 2, it is apparent that in the case where DMSO or DMF was used as a reaction solvent in place of THF, the reactivity was dramatically increased.

Further, as is apparent from the above results, in the case where DMSO was used as a reaction solvent, the amount of TBAF to be used and also the amount of reaction solvent to be used could be reduced. The amount of TBAF to be used could be reduced to about one-fifth compared with the case where THF was used as a reaction solvent. This reveals not only that the amount of expensive TBAF to be used can be reduced, but also that the amount of ethanol used for precipitating the final product can be reduced.

INDUSTRIAL APPLICABILITY

It has become possible to produce an oligo-RNA (A) in a large amount at a high purity through a process for producing an oligonucleic acid derivative in which a protecting group for the 2'-hydroxyl group of each ribose of an oligonucleic acid derivative is removed using a sulfoxide-based solvent or an amide-based solvent or a mixture thereof as a reaction solvent in the step of removing a protecting group for the 2'-hydroxyl group of each ribose by allowing TBAF to act thereon.

I claim:

1. A method for producing an oligonucleic acid derivative of formula (11), comprising the step of:
   reacting (a) tetra-n-butylammonium fluoride (TBAF) and (b) a sulfoxide-based solvent or an amide-based solvent or a mixture thereof, each of which optionally contains THF,
   wherein the sulfoxide-based solvent represents dimethylsulfoxide or ethyl methyl sulfoxide; and
   the amide-based solvent represents N,N-dimethylformamide, N,N-diethylformamide, N,N-dimethylacetamide, N,N-diethylacetamide or N-methylpyrrolidone;
   with an oligonucleic acid derivative of formula (10)

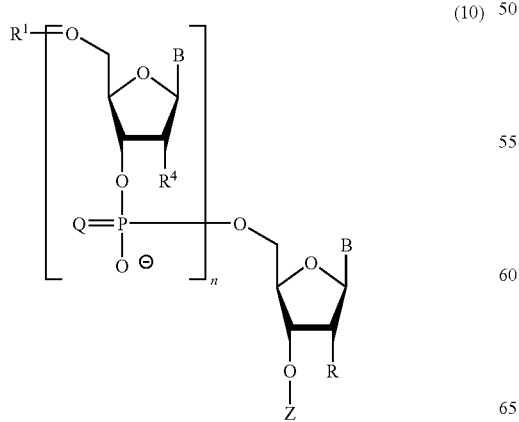

to produce the oligonucleic acid derivative (11)

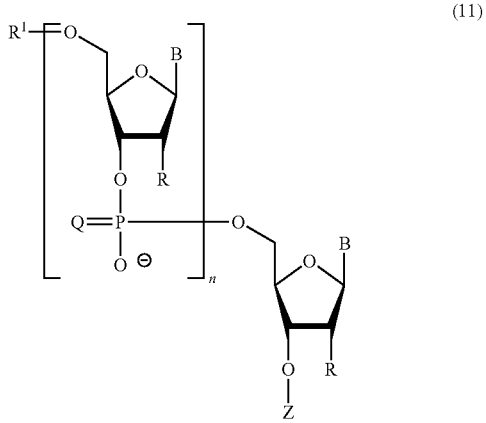

wherein, in formulae (10) and (11), each B independently represents a nucleobase;

n is 1 to 200;

each Q independently represents O or S;

each R independently represents H, hydroxyl, halogen, alkoxy, alkylthio, alkylamino, dialkylamino, alkenyloxy, alkenylthio, alkenylamino, dialkenylamino, alkynyloxy, alkynylthio, alkynylamino, dialkynylamino or alkoxyalkyloxy, and at least one R is hydroxyl;

Z represents H, a phosphate group or a thiophosphate group; and $R^1$ represents a substituent of formula (3)

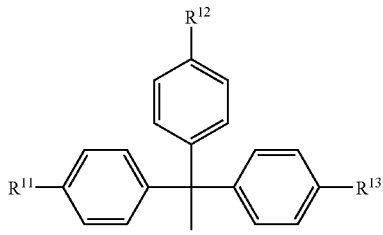

wherein, in formula (3), $R^{11}$, $R^{12}$ and $R^{13}$ are the same or different and each represents hydrogen or alkoxy; and each $R^4$ independently represents H, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or a substituent of formula (4), and at least one $R^4$ is a substituent represented by the following general formula (4)

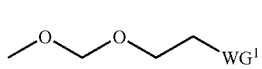

wherein, in the general formula (4), $WG^1$ represents cyano, nitro, alkylsulfonyl, arylsulfonyl or halogen.

2. The method for producing an oligonucleic acid derivative according to claim 1, wherein the sulfoxide-based solvent is dimethylsulfoxide.

3. The method for producing an oligonucleic acid derivative according to claim 1, wherein the amide-based solvent is N,N-dimethylformamide.

4. The method for producing an oligonucleic acid derivative according to claim 1, wherein $WG^1$ is cyano.

5. The method for producing an oligo-RNA according to claim 1, wherein the reaction solvent further contains nitroalkane, alkylamine, amidine, methanethiol, ethanethiol, 1-propanethiol, 1-butanthiol, 1-pentanethiol, 1-hexanthiol, 2-mercaptoethanol, 4-mercapto-1-butanol, 6-mercapto-1-hexanol, mercaptomethyl ether, 2-mercaptoethyl ether, 3-mercaptopropyl ether, 4-mercaptobutyl ether, 5-mercaptopentyl ether, 6-mercaptohexyl ether, or a mixture thereof.

6. The method for producing an oligo-RNA of formula (A),

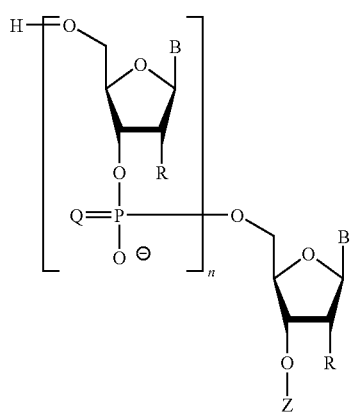

including the step of:
reacting (a) tetra-n-butylammonium fluoride (TBAF) and (b) a sulfoxide-based solvent or an amide-based solvent or a mixture thereof, each of which optionally contains THF, with an oligonucleic acid derivative of formula (10)

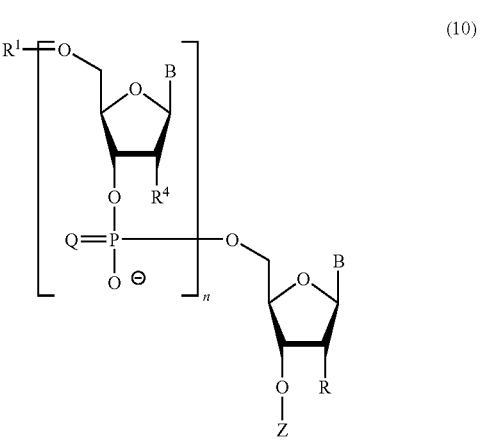

to produce the oligonucleic acid derivative (11)

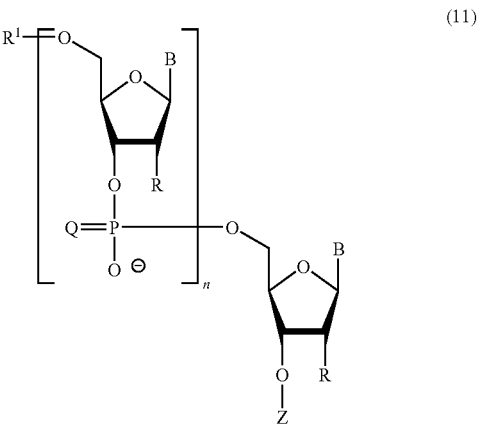

wherein, in formula (A), (10) and (11), each B independently represents a nucleobase;
n is 1 to 200;
each Q independently represents O or S;
each R independently represents H, hydroxyl, halogen, alkoxy, alkylthio, alkylamino, dialkylamino, alkenyloxy, alkenylthio, alkenylamino, dialkenylamino, alkynyloxy, alkynylthio, alkynylamino, dialkynylamino or alkoxyalkyloxy, and at least one R is hydroxyl;
Z represents H, a phosphate group or a thiophosphate group;
$R^1$ represents a substituent of formula (3)

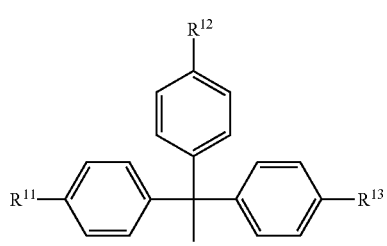

wherein, in formula (3), $R^{11}$, $R^{12}$ and $R^{13}$ are the same or different and each represents hydrogen and each R⁴ independently represents H, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or a substituent of formula (4), and at least one R⁴ is a substituent represented by the following general formula (4)

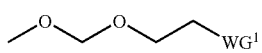

(4)

wherein, in formula (4), WG¹ represents cyano, nitro, alkylsulfonyl, arylsulfonyl or halogen.

7. The method for producing an oligo-RNA according to claim 6, wherein the sulfoxide-based solvent is dimethylsufoxide.

8. The method for producing an oligo-RNA according to claim 6, wherein the amide-based solvent is N,N-dimethylformamide.

9. The method for producing an oligo-RNA according to claim 6, wherein WG¹ is cyano.

10. The method for producing an oligo-RNA according to claim 6, wherein the reaction solvent further contains nitroalkane, alkylamine, amidine, methanethiol, ethanethiol, 1-propanethiol, 1-butanthiol, 1-pentanethiol, 1-hexanthiol, 2-mercaptoethanol, 4-mercapto-1-butanol, 6-mercapto-1-hexanol, mercaptomethyl ether, 2-mercaptoethyl ether, 3-mercaptopropyl ether, 4-mercaptobutyl ether, 5-mercaptopentyl ether or 6-mercaptohexyl ether or a mixture thereof.

11. The method for producing an oligo-RNA of formula (A), comprising the steps of:

(a) reacting an acid with an (oligo)nucleic acid derivative of formula (1)

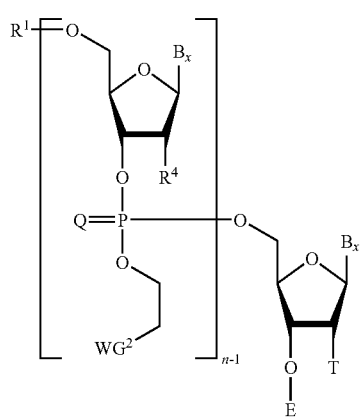

(1)

to produce an (oligo)nucleic acid derivative of formula (2),

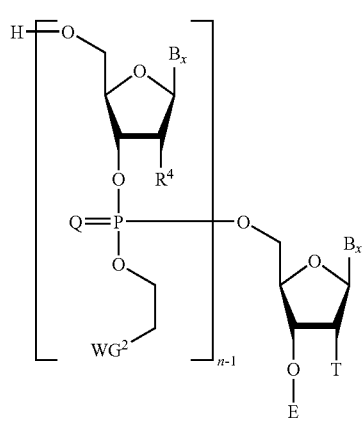

(2)

(b) adding an activating agent to condense a nucleic acid monomer compound with (oligo)nucleic acid derivative (2) to produce an oligonucleic acid derivative of formula (7),

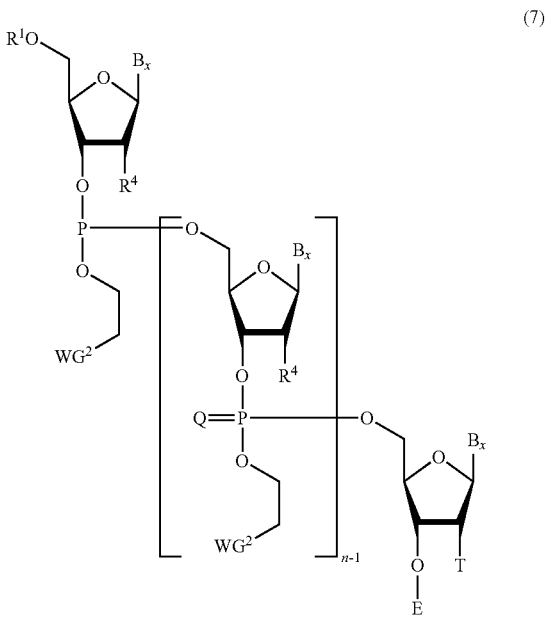

(7)

(c) capping the 5'-hydroxyl group of the unreacted (oligo) nucleic acid derivative of formula (2) from Step (b) to produce an oligonucleic acid derivative of formula (8), (8)

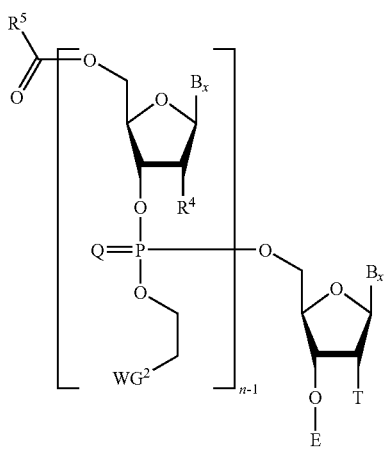

(d) reacting the oligonucleic acid derivative (7) produced in Step (b) with an oxidizing agent to produce an oligonucleic acid derivative of formula (9), (9)

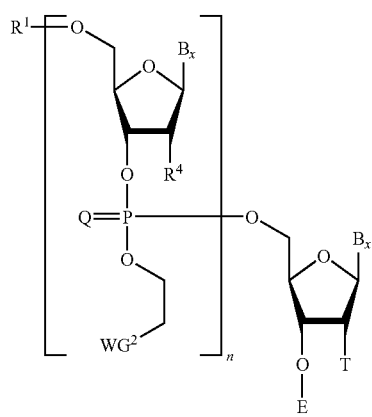

(e) removing the protecting groups of each nucleobase and each phosphate group from oligonucleic acid derivative (9) to produce oligonucleic acid derivative (10), (10)

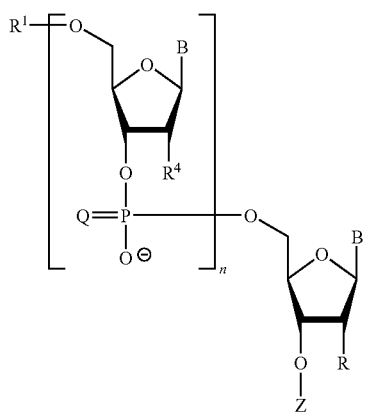

(f) reacting a sulfoxide-based solvent or an amide-based solvent or a mixture thereof, wherein the solvent or mixture optionally contains THF, with an oligonucleic acid derivative of formula (10) to produce an oligonucleic acid derivative of formula (11), (11)

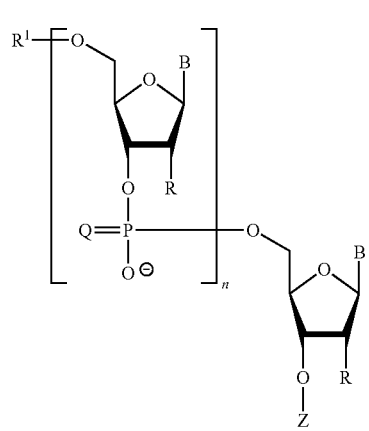

(g) removing the 5'-hydroxyl group of the oligonucleic acid derivative (11) to produce an oligo-RNA of formula (A), and (A)

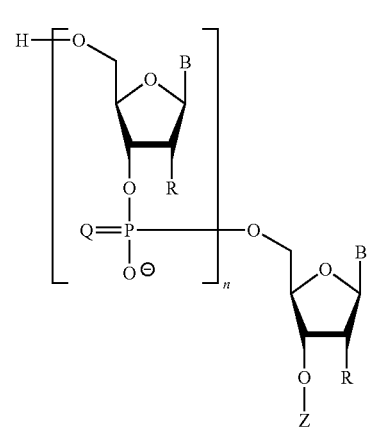

(h) isolating and purifying the oligo-RNA (A) produced by Step (g)

wherein, formulae (1), (2), (7), (8), (9), (10), (11), and (A), each B independently represents a nucleobase;

each $B_x$ independently represents a nucleobase optionally substituted with one or more protecting groups;

n is 1 to 200;

each Q independently represents O or S;

each R independently represents H, hydroxyl, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, or alkoxyalkyloxy, and at least one R is hydroxyl;

Z represents H, a phosphate group or a thiophosphate group;

$R^1$ represents a substituent of formula (3)

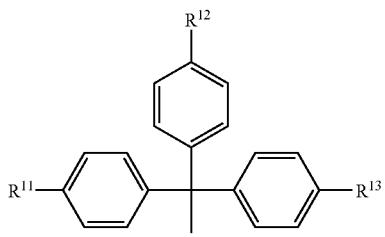

(3)

wherein, in formula (3), $R^{11}$, $R^{12}$ and $R^{13}$ are the same or different and each represents hydrogen or alkoxy;
each $WG^2$ represents cyano, nitro, alkylsulfonyl, arylsulfonyl or halogen;
each $R^4$ independently represents H, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy or a substituent of formula (4), and at least one $R^4$ is a substituent represented by the following general formula (4)

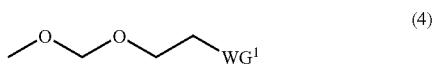

(4)

wherein, in formula (4), $WG^1$ represents cyano, nitro, alkylsulfonyl, arylsulfonyl or halogen;
E represents acyl or a substituent of formula (5)

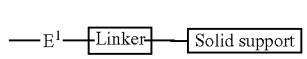

(5)

wherein, in formula (5), $E^1$ represents a single bond or a substituent of formula (6)

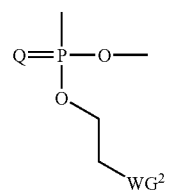

(6)

wherein, in formula (6), Q and $WG^2$ have the same meanings as above;
T represents H, acyloxy, halogen, alkoxy, alkylthio, alkylamino, dialkylamino, alkenyloxy, alkenylthio, alkenylamino, dialkenylamino, alkynyloxy, alkynylthio, alkynylamino, dialkynylamino, alkoxyalkyloxy, a substituent of formula (4) or a substituent of formula (5), with the proviso that either E or T is a substituent (5);
$R^5$ represents methyl, phenoxymethyl, or tert-butylphenoxymethyl; the sulfoxide-based solvent represents dimethylsulfoxide or ethyl methyl sulfoxide; and the amide-based solvent represents N,N-dimethylformamide, N,N-diethylformamide, N,N-dimethylacetamide, N,N-diethylacetamide or N-methylpyrrolidone.

12. The method for producing an oligo-RNA according to claim 11, comprising repeating steps (a) to (d).

13. The method for producing an oligo-RNA according to claim 11, comprising adding one or more units of a compound of formula (B) as a nucleic acid monomer compound in Step (b)

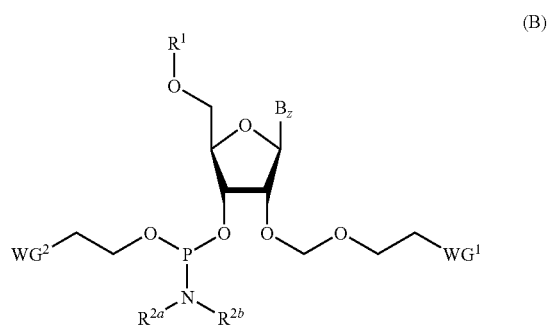

(B)

wherein, in formula (B), $B_Z$ represents a nucleobase optionally substituted with a protecting group;
$R^1$ represents a substituent of formula (3)

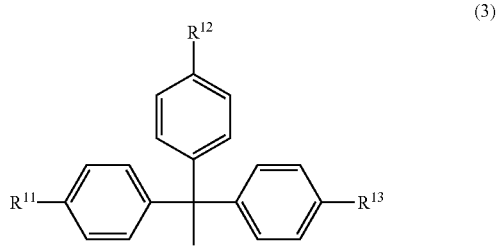

(3)

wherein, in formula (3), $R^{11}$, $R^{12}$ and $R^{13}$ are the same or different and each represents hydrogen or alkoxy;
$R^{2a}$ and $R^{2b}$ are the same or different and each represents alkyl, or $R^{2a}$ and $R^{2b}$, together with the adjacent nitrogen atom, may form a 5- or 6-membered saturated cyclic amino group,
wherein the cyclic amino group optionally has one oxygen atom or one sulfur atom as a ring-composing member in addition to the adjacent nitrogen atom; and
$WG^1$ and $WG^2$ are the same or different and each represents cyano, nitro, alkylsulfonyl, arylsulfonyl or halogen.

14. The method for producing the oligo-RNA according to claim 11, wherein the sulfoxide-based solvent is dimethylsulfoxide.

15. The method for producing the oligo-RNA according to claim 11, wherein the amide-based solvent is N,N-dimethylformamide.

16. The method for producing an oligo-RNA according to claim 11, wherein $WG^1$ is cyano.

17. The method for producing an oligo-RNA according to claim 11, wherein the solvent in step (f) further contains nitroalkane, alkylamine, amidine, methanethiol, ethanethiol, 1-propanethiol, 1-butanethiol, 1-pentanethiol, 1-hexanthiol, 2-mercaptoethanol, 4-mercapto-1-butanol, 6-mercapto-1-hexanol, mercaptomethyl ether, 2-mercaptoethyl ether, 3-mercaptopropyl ether, 4-mercaptobutyl ether, 5-mercaptopentyl ether or 6-mercaptohexyl ether or a mixture thereof.

* * * * *